(12) United States Patent
Du et al.

(10) Patent No.: US 7,378,434 B2
(45) Date of Patent: *May 27, 2008

(54) METAXALONE PRODUCTS, METHOD OF MANUFACTURE, AND METHOD OF USE

(75) Inventors: Jie Du, Lansdale, PA (US); Richard H. Roberts, Lakewood, NJ (US)

(73) Assignee: Mutual Pharmaceutical Company, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/483,332

(22) Filed: Jul. 7, 2006

(65) Prior Publication Data

US 2007/0088066 A1    Apr. 19, 2007

Related U.S. Application Data

(63) Continuation of application No. 11/364,468, filed on Feb. 28, 2006, now Pat. No. 7,122,566, which is a continuation of application No. 11/349,534, filed on Feb. 6, 2006.

(60) Provisional application No. 60/726,861, filed on Oct. 14, 2005.

(51) Int. Cl.
  *A61K 31/42* (2006.01)
(52) U.S. Cl. .................................... 514/376
(58) Field of Classification Search ............... None
  See application file for complete search history.

(56) References Cited

U.S. PATENT DOCUMENTS

| 6,407,128 | B1 | 6/2002 | Scaife et al. | |
|---|---|---|---|---|
| 6,683,102 | B2 | 1/2004 | Scaife et al. | |
| 7,122,566 | B1 * | 10/2006 | Du et al. | 514/376 |
| 2004/0265889 | A1 | 12/2004 | Durham et al. | |

OTHER PUBLICATIONS

Medline Abstract No. 97217050, Kumar, Indian Journal of Experimental Biology, (May 1996) 34(5), 391-402.*
Medline Abstract No. 96432582, Oka et al., Japanese Journal of Pharmacology, (Jun. 1996) 71(2), 89-100.*
Medline Abstract No. 97074593, Smith et al., CA: A Cancer Journal for Clinicians, (Nov.-Dec. 1996), 46(6), 343-63.*
Medline Abstract No. 1998029329, Rickels et al., Journal of Clinical Psychiatry, (1997) 58 Suppl. 11, 4-10.*
Bynum, N.D., et al "Postmortem Distribution of Tramadol, Amitriptyline, and Their Metabolites in a Suicidal Overdose", Journal of Analytical Toxicology, 29(5): 401-406 (2005).
Chou, R., et al "Comparative Efficacy and Safety of Skeletal Muscle Relaxants for Spasticity and Musculoskeletal Conditions: A systematic Review", J. Pain Symptom Management 28(2):140-75 (2004).
Elenbaas, J. K. "Centrally Acting Oral Skeletal Muscle Relaxants", Am J Hosp Pharm. 37(10):1313-1323 (1980).

Gruszecki, A.C., et al "Polydrug Fatality Involving Metaxalone", J. Forensic Science 48(2): 432-4 (2003).
Kuykendall, J.R., et al "Auditory Hallucinations Elicited by Combined Meclizine and Metaxalone Use at Bedtime", Ann. Pharmacother. 38(11): 1968-1969 (2004).
Moore, K.A., et al "A Fatality Involving Metaxalone", Forensic Sci Int. 149 (2-3): 249-251 (2005).
Obach, R. S., et al "Human Liver Aldehyde Oxidase: Inhibition by 239 Drugs", Journal of Clinical Pharmacology 44(1): 7-19 (2004).
Poklis, J. L., et al "Metaxalone (Skelaxin)-Related Death", Journal of Analytical Toxicology 28(6): 537-540 (2004).
Schafer, Jr., E.W., et al "The Acute Oral Toxicity, Repellency, and Hazard Potential of 998 Chemicals to One or More Species of Wild and Domestic Birds", Archives of Environmental Contamination and Toxicology 12(3): 355-382 (1983).
Seidler, J., "Identification and Prediction of Promiscuous Aggregating Inhibitors Among Known Drugs", Journal of Medicinal Chemistry, 46(21): 4477-4486 (2003).
Toth, P.P., et al "Commonly Used Muscle Relaxant Therapies for Acute Low Back Pain: A Review of Carisoprodol, Cyclobenzaprine Hydrochloride, and Metaxalone", Clinical Therapeutics, 26(9): 1355-1367 (2004).
Prescribing Information for Skelaxin (metaxalone) as accessed at www.kingpharm.com on Dec. 21, 2005.
Sahi, J. et al "Comparative Effects of Thiazolidinediones on In Vitro P450 Enzyme Induction And Inhibition", The American Soc. For Pharmacology and Experimental Therapeutics, 31(4): 439-446 (2003).
"Norvir (ritonavir sulfate)", *Physicians' Desk Reference*, 58th Edition, 2004, Montvale, NJ, Thomson PDR, pp. 496-503.
"Crixivan.(indinavir sulfate)", *Physicians' Desk Reference*, 58th Edition, 2004, Montvale, NJ, Thomson PDR, pp. 1957-1962.
Bynum ND, et al., "Postmortem Distribution of Tramadol, Amitriptyline, and Their Metabolites in a Suicidal Overdose" Journal of Analytical Toxicology, 29(5): 401-406 (2005).
Chou R, et al., "Comparative Efficacy and Safety of Skeletal Muscle Relaxants for Spasticity and Musculoskeletal Conditions: A Systematic Review", J. Pain Symptom Management 28(2):140-75 (2004).
Elenbaas JK, "Centrally Acting Oral Skeletal Muscle Relaxants," Am J Hosp Pharm. 37(10): 1313-1323 (1980).
Gruszecki AC, et al., "Polydrug Fatality Involving Metaxalone," J. Forensic Science 48(2): 432-4 (2003).

(Continued)

*Primary Examiner*—Raymond J Henley, III
(74) *Attorney, Agent, or Firm*—Cantor Colburn LLP

(57) ABSTRACT

Disclosed herein is a method of using metaxalone. In one embodiment, the method comprises obtaining metaxalone from a container providing information that metaxalone affects the activity of a cytochrome p450 isozyme. In another embodiment, the method comprises informing a user that metaxalone affects the activity of a cytochrome p450 isozyme. Also included are articles of manufacture comprising a container containing a dosage form of metaxalone, wherein the container is associated with published material informing that metaxalone affects activity of a cytochrome p450 isozyme. Also disclosed are a method of treatment and a method of manufacturing a metaxalone product.

8 Claims, No Drawings

OTHER PUBLICATIONS

Kuykendall JR, and Rhodes RS, "Auditory Hallucinations Elicited by Combined Meclizine and Metaxalone Use at Bedtime," Ann. Pharmacother. 38(11): 1968-1969 (2004).

Moore KA, et al., "A Fatality Involving Metaxalone", Forensic Sci Int. 149 (2-3): 249-251 (2005).

Obach, RS, "Human Liver Aldehyde Oxidase: Inhibition by 239 Drugs", Journal of Clinical Pharmacology 44 (1):7-19.

Poklis JL, et al., "Metaxalone (Skelaxin)-Related Death", Journal of Analytical Toxicology 28 (6): 537-540 (2004).

Schafer EW, et al., "The Acute Oral Toxicity, Repellency, and Hazard Potential of 998 Chemicals to One or More Species of Wild and Domestic Birds", Archives of Environmental Contamination and Toxicology 12(3): 355-382 (1983).

Seidler, J, et al., "Identification and Prediction of Promiscuous Aggregating Inhibitors Among Known Drugs", Journal of Medicinal Chemistry, 46 (21):, 4477-4486 (2003).

Toth, PP, and Urtis J, "Commonly Used Muscle Relaxant Therapies for Acute Low Back Pain: A Review of Carisoprodol, Cyclobenzaprine Hydrochloride, and Metaxalone," Clinical Therapeutics, 26(9): 1355-1367 (2004).

Prescribing Information for Skelaxin (metaxalone) as accessed at www.kingpharm.com on Dec. 21, 2005.

* cited by examiner

METAXALONE PRODUCTS, METHOD OF MANUFACTURE, AND METHOD OF USE

CROSS REFERENCE TO RELATED APPLICATION

This application is a continuation of U.S. application Ser. No. 11/364,468 filed Feb. 28, 2006, now U.S. Pat. No. 7,122,566, which is a continuation of U.S. application Ser. No. 11/349,534 filed Feb. 6, 2006, which claims the benefit of U.S. Provisional Application Ser. No. 60/726,861 filed Oct. 14, 2005, all of which are hereby incorporated by reference in their entirety.

BACKGROUND

This application relates to metaxalone products for therapeutic purposes, and in particular to improved methods of use of metaxalone.

Metaxalone, 5-[(3,5-dimethylphenoxy) methyl]-2-oxazolidinone, is used as a skeletal muscle relaxant. The mechanism of action of metaxalone in humans has not been established but may be due to general central nervous system depression.

Metaxalone was approved by the U.S. Food and Drug Administration (FDA) in 1962 as an adjunct to rest, physical therapy, and other measures for the relief of discomforts associated with acute, painful musculoskeletal conditions, such as muscles in spasm. Metaxalone is marketed in the United States under the brand name SKELAXIN®. The dosage forms currently approved for marketing are tablets containing 400 milligrams (mg) or 800 mg of metaxalone. The currently recommended dose for adults and children over 12 years of age is 800 mg, three to four times a day.

Food can affect gastric emptying, and may also alter the release of an active agent from a dosage form, the solubilization of the active agent, and the transport of the active agent across the intestinal wall. For lipophilic, water-insoluble active agents, fatty meals can increase gastric residence time thereby increasing the time available for solubilization and also may enhance the solubilization of the active agent by the lipids contained in the meal. According to U.S. Pat. No. 6,407,128, evaluation of the effect of food on the pharmacokinetics of metaxalone showed that food increased the rate and extent of absorption of a 400 mg oral dosage form in humans.

Studies directed to possible interactions of metaxalone with other active agents have been limited. There have been no detailed studies of the specific enzymes involved in metabolism of metaxalone or of the inhibitory or inducing effects of metaxalone on any Phase I or Phase II metabolic enzymes. In particular, there appear to be no published studies of the inhibitory and inducing effects of metaxalone on particular human cytochrome p450 isozymes or the possible metabolism of metaxalone by particular human cytochrome p450 isozymes.

Several major enzymes and pathways are involved in drug metabolism. Pathways of drug biotransformation are usually divided into two major groups of reactions: Phase I and Phase II metabolism.

Some typical examples of Phase I metabolism include oxidation, hydrolysis and reduction. Examples of Phase I enzymes involved in oxidation reactions are the cytochrome p450 monooxygenase system, the flavin-containing monooxygenase system, alcohol dehydrogenase and aldehyde dehydrogenase, monoamine oxidase, and peroxidases for co-oxidation. Examples of Phase I enzymes involved in reduction are NADPH-cytochrome p450 reductase and reduced (ferrous) cytochrome p450. Examples of Phase I hydrolysis enzymes are epoxide hydrolase, esterases and amidases.

Phase II metabolism involves conjugation reactions. Typical conjugation reactions are glucuronidation, sulfation, amino acid conjugation, acetylation, methylation, and mercapturic acid conjugation. Examples of Phase II metabolic enzymes are glutathione S-transferases (GSTs), mercapturic acid biosynthetic enzymes (transpeptidases, peptidases, and N-acetylases), UDP-glucoron(os)yltransferases, N-acetyltransferases, amino acid N-acyl transferases, and sulfotransferases.

One of the most important groups of Phase I enzymes are the cytochrome p450 monooxygenase system enzymes. The cytochrome p450 enzymes are a highly diverse superfamily of enzymes. NADPH is required as a coenzyme and oxygen is used as a substrate. Each enzyme is termed an isoform or isozyme since each derives from a different gene.

Many members of the cytochrome p450 family are known to metabolize active agents in humans. Active agent interactions associated with metabolism by cytochrome p450 isoforms generally result from enzyme inhibition or enzyme induction. Enzyme inhibition often involves competition between two active agents for the substrate binding site of the enzyme, although other mechanisms for inhibition exist. Enzyme induction occurs when an active agent activates an enzyme or stimulates the synthesis of more enzyme protein, enhancing the enzyme's metabolizing capacity.

Cytochrome p450 isozymes identified as important in active agent metabolism are CYP1A2, CYP2A6, CYP2B6, CYP2C9, CYP2C19, CYP2D6, CYP2E1, and CYP3A4. Examples of cytochrome p450 enzymes known to be involved in active agent interactions are the CYP3A subfamily, which is involved in many clinically significant active agent interactions, including those involving non-sedating antihistamines and cisapride, and CYP2D6, which is responsible for the metabolism of many psychotherapeutic agents, such as thioridazine. CYP3A4 and CYP1A2 enzymes are involved in active agent interactions involving theophylline. CYP2C9, CYP1A2, and CYP2C19 are involved in active agent interactions involving warfarin. Phenytoin and fosphenytoin are metabolized by CYP1A2, CYP2C9, CYP2C19, and CYP3A4; mexiletine is metabolized by CYP2D6 and CYP1A2; and propafenone is metabolized by CYP2D6, CYP3A4, and CYP1A2.

Additionally, several cytochrome p450 isozymes are known to be genetically polymorphic, leading to altered substrate metabolizing ability in some individuals. Allelic variants of CYP2D6 are the best characterized, with many resulting in an enzyme with reduced, or no, catalytic activity. Gene duplication also occurs. As a result, four phenotypic subpopulations of metabolizers of CYP2D6 substrates exist: poor (PM), intermediate (IM), extensive (EM), and ultrarapid (UM). The genetic polymorphisms vary depending on the population in question. For example, Caucasian populations contain a large percentage of individuals who are poor metabolizers, due to a deficiency in CYP2D6—perhaps 5-10% of the population, while only 1-2% of Asians are PMs. CYP2C9, which catalyzes the metabolism of a number of commonly used active agents, including that of warfarin and phenytoin, is also polymorphic. The two most common CYP2C9 allelic variants have reduced activity (5-12%) compared to the wild-type enzyme. Genetic polymorphism also occurs in CYP2C19, for which at least 8 allelic variants have been identified that result in catalytically inactive protein. About 3% of Caucasians are poor metabolizers of active agents metabolized by CYP2C19, while 13-23% of Asians are poor metabolizers of active agents metabolized by CYP2C19.

By understanding the unique functions and characteristics of Phase I and Phase II metabolic enzymes, physicians may better anticipate and manage active agent interactions and may predict or explain an individual's response to a particular therapeutic regimen.

There accordingly remains a need in the art for improved methods for the administration and use of metaxalone, in particular methods that take into account the effects of metaxalone on activity of Phase I and Phase II metabolic enzymes, including the cytochrome P450 isozymes.

SUMMARY

Disclosed herein are methods of using metaxalone. Metaxalone can be used in the treatment of various diseases or conditions, including, for example, musculoskeletal conditions and head pain.

In one embodiment, the method comprises informing a user that metaxalone affects the activity of a cytochrome p450 isozyme.

In another embodiment, the method comprises informing a user that metaxalone is metabolized by a cytochrome p450 isozyme.

In another embodiment, the method comprises informing a user that metaxalone inhibits a cytochrome p450 isozyme.

In yet another embodiment, the method comprises informing a user that metaxalone induces a cytochrome p450 isozyme.

In another embodiment, the method comprises informing a user that metaxalone affects activity of a cytochrome p450 isozyme and that administration of metaxalone with a substance can affect the plasma concentration, bioavailability, safety, efficacy, or a combination comprising at least one of the foregoing of metaxalone or the substance.

In another embodiment, the method comprises informing a user that metaxalone is metabolized by CYP1A2 or CYP3A4; and that there is a potential active agent interaction for metaxalone with an active agent that is a substrate, inhibitor, or inducer of CYP1A2 or CYP2C19 or that taking metaxalone with the active agent can affect the plasma concentration, bioavailability, safety, efficacy, or a combination comprising at least one of the foregoing of metaxalone or the active agent.

In another embodiment, the method comprises informing a user that metaxalone is an inhibitor or an inducer of a cytochrome p450 isozyme and administration of metaxalone with a substance that is a substrate of the cytochrome p450 isozyme can affect the plasma concentration, bioavailability, safety, efficacy, or a combination comprising at least one of the foregoing of the substance.

In yet another embodiment, the method comprises obtaining metaxalone from a container providing information that metaxalone affects activity of a cytochrome p450 isozyme.

In yet another embodiment, the method comprises obtaining metaxalone from a container providing information that metaxalone is metabolized by a cytochrome p450 isozyme.

In yet another embodiment, the method comprises obtaining metaxalone from a container providing information that metaxalone is an inhibitor or an inducer of a cytochrome p450 isozyme.

In yet another embodiment, the method comprises administering to a patient metaxalone and an active agent; and informing the patient that metaxalone affects activity of a cytochrome p450 isozyme.

In yet another embodiment, the method comprises informing a user that metaxalone affects activity of a cytochrome p450 isozyme; that administration of metaxalone with a substance can affect the plasma concentration, bioavailability, safety, efficacy, or a combination comprising at least one of the foregoing of metaxalone or the substance; and that any effect on the plasma concentration, bioavailability, safety, efficacy, or a combination comprising at least one of the foregoing of metaxalone or the substance can vary with administration of metaxalone with or without food.

In another embodiment, the method comprises obtaining metaxalone from a container providing information that metaxalone affects activity of a cytochrome p450 isozyme; that administration of metaxalone with a substance can affect the plasma concentration, bioavailability, safety, efficacy, or a combination comprising at least one of the foregoing of metaxalone or the substance; and that any effect on the plasma concentration, bioavailability, safety, efficacy, or a combination comprising at least one of the foregoing of metaxalone or the substance can vary with administration of metaxalone with or without food.

Also disclosed herein are methods of manufacturing a metaxalone product.

In one embodiment, the method comprises packaging a metaxalone dosage form with information that metaxalone affects activity of a cytochrome p450 isozyme.

In another embodiment, the method comprises packaging a metaxalone dosage form with information that metaxalone is metabolized by a cytochrome p450 isozyme.

In another embodiment, the method comprises packaging a metaxalone dosage form with information that metaxalone is an inhibitor or an inducer of a cytochrome p450 isozyme.

In yet another embodiment, the method comprises packaging a metaxalone dosage form with information that metaxalone affects activity of a cytochrome p450 isozyme; that administration of metaxalone with a substance can affect the plasma concentration, safety, or efficacy of the metaxalone or the substance; and that any effect on the plasma concentration, bioavailability, safety, efficacy, or a combination comprising at least one of the foregoing of metaxalone or the substance can vary with administration of metaxalone with or without food.

Also disclosed herein are articles of manufacture comprising a container containing a dosage form of metaxalone.

In one embodiment, the container is associated with published material informing that metaxalone affects activity of a cytochrome p450 isozyme.

In another embodiment, the container is associated with published material informing that metaxalone is metabolized by a cytochrome p450 isozyme.

In another embodiment, the container is associated with published material informing that metaxalone is an inhibitor or an inducer of a cytochrome p450 isozyme.

In yet another embodiment, the container is associated with published material informing that metaxalone affects activity of a cytochrome p450 isozyme; that administration to a patient of metaxalone with a substance can affect plasma concentration, bioavailability, safety, efficacy, or a combination comprising at least one of the foregoing of metaxalone or the substance; and that any effect on the plasma concentration, bioavailability, safety, efficacy, or a combination comprising at least one of the foregoing of metaxalone or the substance can vary with administration of metaxalone with or without food.

In yet another embodiment, the article comprises a container comprising a dosage form of metaxalone, and published material. In one embodiment, the published material informs that there is a potential active agent interaction with warfarin; or that administration with warfarin can affect the plasma concentration, bioavailability, safety, efficacy, or a combination comprising at least one of the foregoing of metaxalone or warfarin. In another embodiment, the published material informs that metaxalone is a substrate of CYP1A2 or CYP2C19, or that metaxalone is an inhibitor of CYP1A2, CYP2B6, CYP2C9, CYP2C19, CYP2D6, CYP2E1, or CYP3A4, or that metaxalone is an inducer of CYP1A2 or CYP3A4.

Also disclosed herein is an article of manufacture comprising packaging material and a product contained within the packaging material, wherein the product comprises, as at least one active ingredient, metaxalone, and wherein the packaging material comprises a label approved by a regulatory agency for the product which states that metaxalone affects activity of a cytochrome p450 isozyme.

Also disclosed herein is a method of using an active agent that is a known substrate, inhibitor, or inducer of CYP1A2 or CYP2C19 or a substrate of a cytochrome p450 isozyme.

In one embodiment, the method comprises informing a user that metaxalone affects activity of a cytochrome p450 isozyme and that administration of the active agent with metaxalone can affect the plasma concentration, bioavailability, safety, efficacy, or a combination comprising at least one of the foregoing of the active agent or metaxalone.

In another embodiment, the method comprises obtaining an active agent that is a known substrate, inhibitor, or inducer of CYP1A2 or CYP2C19 or a substrate of a cytochrome p450 isozyme from a container providing information that metaxalone affects activity of a cytochrome p450 isozyme and that administration of the active agent with metaxalone can affect plasma concentration, bioavailability, safety, efficacy, or a combination comprising at least one of the foregoing of the active agent or metaxalone.

Also disclosed herein is a method of manufacturing a pharmaceutical product comprising an active agent that is a known substrate, inhibitor, or inducer of CYP1A2 or CYP2C19 or a substrate of a cytochrome p450 isozyme.

In one embodiment, the method comprises packaging a dosage form of the active agent that is a known substrate, inhibitor, or inducer of CYP1A2 or CYP2C19 or a substrate of a cytochrome p450 isozyme with information that metaxalone affects activity of a cytochrome p450 isozyme and that administration of the active agent with metaxalone can affect plasma concentration, bioavailability, safety, efficacy, or a combination comprising at least one of the foregoing of the active agent or metaxalone.

Also disclosed herein is an article of manufacture comprising a container containing a dosage form of an active agent that is a known substrate, inhibitor, or inducer of CYP1A2 or CYP2C19 or a substrate of a cytochrome p450 isozyme. The container is associated with published material informing that metaxalone affects activity of a cytochrome p450 isozyme and that administration to a patient of the active agent and metaxalone can affect plasma concentration, bioavailability, safety, efficacy, or a combination comprising at least one of the foregoing of the active agent or metaxalone.

These and other embodiments, advantages and features of the present invention become clear when detailed description and examples are provided in subsequent sections.

DETAILED DESCRIPTION

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including metaxalone), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound or salt, crystalline forms, non-crystalline forms, and any polymorphs of the compound are included. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, free compound and salts of an active agent) of metaxalone or other active agent may be employed either alone or in combination.

"Active agent interaction" refers to a change in the metabolism of an active agent in a patient that can occur with co-administration of a second active agent. A "potential active agent interaction" refers to an active agent interaction between two active agents that is theoretically possible based on knowledge that one of the active agents is metabolized by a given cytochrome p450 isozyme and that the second of the active agents is a substrate, inhibitor, or inducer of that cytochrome p450 isozyme.

"Administering metaxalone with a substance" means metaxalone and the substance are administered simultaneously in a single dosage form, administered concomitantly in separate dosage forms, or administered in separate dosage forms separated by some amount of time that is within the time in which both metaxalone and the substance are within the blood stream of a patient. The metaxalone and the substance need not be prescribed for a patient by the same medical care worker. The substance need not require a prescription. Administration of metaxalone or the substance can occur via any appropriate route, for example, oral tablets, oral capsules, oral liquids, inhalation, injection, suppositories or topical contact.

"Affects" include an increase or decrease in degree, level, or intensity; a change in time of onset or duration; a change in type, kind, or effect, or a combination comprising at least one of the foregoing.

As used herein, "allelic variant" means one of the alternative forms at a genetic locus on a single chromosome. For loci in most of the human genome, a human has two chromosomes, which may carry the same or two different allelic variants.

"Altering the dose of an active agent" can mean tapering off, reducing or increasing the dose of the active agent, ceasing to administer the active agent to the patient, or substituting a second active agent for the active agent.

"Bioavailability" means the extent or rate at which an active agent is absorbed into a living system or is made available at the site of physiological activity. For active agents that are intended to be absorbed into the bloodstream, bioavailability data for a given formulation may provide an estimate of the relative fraction of the administered dose that is absorbed into the systemic circulation. "Bioavailability" can be characterized by one or more pharmacokinetic parameters.

A "dosage form" means a unit of administration of an active agent. Examples of dosage forms include tablets, capsules, injections, suspensions, liquids, emulsions, creams, ointments, suppositories, inhalable forms, transdermal forms, and the like.

The term "effective amount" or "therapeutically effective amount" means an amount effective, when administered to a patient, to provide any therapeutic benefit. A therapeutic benefit may be an amelioration of symptoms, e.g., an amount effective to decrease the symptoms of an acute musculoskeletal condition, such as muscle spasms. In certain circumstances a patient may not present symptoms of a condition for which the patient is being treated. A therapeutically effective amount of an active agent may also be an amount sufficient to provide a significant positive effect on any indicium of a disease, disorder, or condition, e.g. an amount sufficient to significantly reduce the frequency and severity of muscle spasms. A significant effect on an indicium of a disease, disorder, or condition is statistically significant in a standard parametric test of statistical significance, for example Student's T-test, where $p \leq 0.05$. An "effective amount or "therapeutically effective amount" of metaxalone may also be an amount of about 3600 mg per day or less, about 3200 mg per day or less, about 50 mg to about 3600 mg per day, or of any dosage amount approved by a governmental authority such as the US FDA, for use in treatment. In some embodiments amounts of 3200 mg metaxalone per day, 800 mg metaxalone per unit dosage form, or 400 mg metaxalone or less per unit dosage form is an "effective amount" or "therapeutically effective amount" of metaxalone.

"Efficacy" means the ability of an active agent administered to a patient to produce a therapeutic effect in the patient.

As used herein "food" means a solid food with sufficient bulk and fat content that it is not rapidly dissolved and absorbed in the stomach. More specifically, the food is a meal, such as breakfast, lunch, or dinner. A dosage of metaxalone administered to a patient "with food" or in a "fed" state is administered to the patient between about 30 minutes prior to about 2 hours after eating a meal; more specifically, the dosage is administered within 15 minutes of eating a meal. The terms "without food" or "fasted" are defined to mean the condition of not having consumed solid food for about one hour prior to until about 2 hours after such consumption.

"Head pain" includes any painful conditions of the head, but particularly includes headaches, such as migraines, cluster headaches, tension headaches, or tension related migraines. Head pain further includes painful facial conditions such as TMJ (temporomandibular joint) disorders.

"Informing" means referring to or providing, published material, for example, providing an active agent with published material to a user; or presenting information orally, for example, by presentation at a seminar, conference, or other educational presentation, by conversation between a pharmaceutical sales representative and a medical care worker, or by conversation between a medical care worker and a patient; or demonstrating the intended information to a user for the purpose of comprehension.

As used herein, an enzyme "metabolizing" a substance means the enzyme can chemically transform the substance.

A "medical care worker" means a worker in the health care field who may need or utilize information regarding an active agent, including a dosage form thereof, including information on safety, efficacy, dosing, administration, or pharmacokinetics. Examples of medical workers include physicians, pharmacists, physician's assistants, nurses, aides, caretakers (which can include family members or guardians), emergency medical workers, and veterinarians.

As used herein, "metaxalone therapy" refers to medical treatment of a symptom, disorder, or condition by administration of metaxalone.

The term "musculoskeletal condition" includes any condition affecting the muscles, tendons, ligaments, bones, joints, and associated tissues that move the body and maintain its form. Such conditions include conditions that originate in the muscles, tendons, ligaments, or bones and associated tissues or conditions that originate elsewhere in the body, for example in the central or peripheral nervous system, that are manifested in the muscles, tendons, ligaments, bones, joints or associated tissues.

A substance having a "narrow therapeutic index" (NTI) means a substance falling within any definition of narrow therapeutic index as promulgated by the U.S. Food and Drug Administration or any successor agency thereof, for example, a substance having a less than 2-fold difference in median lethal dose (LD50) and median effective dose (ED50) values, or having a less than 2-fold difference in the minimum toxic concentration and minimum effective concentration in the blood.

"Oral dosage form" includes a dosage form for oral administration.

A "patient" means a human or non-human animal in need of medical treatment. Medical treatment can include treatment of an existing condition, such as a disease or disorder, prophylactic or preventative treatment, or diagnostic treatment. In some embodiments the patient is a human patient.

A "pharmaceutical supplier" means a person (other than a medical care worker), business, charitable organization, governmental organization, or other entity involved in the transfer of active agent, including a dosage form thereof, between entities, for profit or not. Examples of pharmaceutical suppliers include pharmaceutical distributors, pharmacy chains, pharmacies (online or physical), hospitals, HMOs, supermarkets, the Veterans Administration, or foreign businesses or individuals importing active agent into the United States.

"Pharmacokinetic parameters" describe the in vivo characteristics of an active agent (or surrogate marker for the active agent) over time, such as plasma concentration (C), $C_{max}$, $C_n$, $C_{24}$, $T_{max}$, and AUC. "$C_{max}$" is the measured concentration of the active agent in the plasma at the point of maximum concentration. "$C_n$" is the measured concentration of an active agent in the plasma at about n hours after administration. "$C_{24}$" is the measured concentration of an active agent in the plasma at about 24 hours after administration. The term "$T_{max}$" refers to the time at which the measured concentration of an active agent in the plasma is the highest after administration of the active agent. "AUC" is the area under the curve of a graph of the measured concentration of an active agent (typically plasma concentration) vs. time, measured from one time point to another time point. For example $AUC_{0-t}$ is the area under the curve of plasma concentration versus time from time 0 to time t. The $AUC_{0-\infty}$ or $AUC_{0-INF}$ is the calculated area under the curve of plasma concentration versus time from time 0 to time infinity.

"Phenotype" means an observable trait of an organism resulting from the interplay of environment and genetics. Examples include apparent rate of metabolism of substrates by a cytochrome p450 isozyme of an organism, such as the "poor metabolizer" (PM) or "ultrarapid metabolizer" (UM) phenotypes identified in humans for metabolism of substrates metabolized by CYP2D6.

"Polymorphism" means the differences in DNA sequences that occur naturally in a population. Single nucleotide substitutions, insertions, and deletions of nucleotides and repetitive sequences (microsatellites) are all examples of a polymorphism.

A "product" or "pharmaceutical product" means a dosage form of an active agent plus published material, and optionally packaging.

"Providing" means giving, administering, selling, distributing, transferring (for profit or not), manufacturing, compounding, or dispensing.

"Published material" means a medium providing information, including printed, audio, visual, or electronic medium, for example a flyer, an advertisement, a product insert, printed labeling, an internet web site, an internet web page, an internet pop-up window, a radio or television broadcast, a compact disk, a DVD, an audio recording, or other recording or electronic medium.

"Safety" means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

"Salts" as used herein describes "pharmaceutically acceptable salts" of metaxalone and other active agents discussed herein and also includes solvates and hydrates of such active agents. The active agent may be modified by making non-toxic acid or base addition salts thereof. Examples of pharmaceutically acceptable salts include mineral or organic acid addition salts of basic residues such as amines; alkali or organic addition salts of acidic residues; and the like, and combinations comprising one or more of the foregoing salts. The pharmaceutically acceptable salts include non-toxic salts and the quaternary ammonium salts of the metaxalone. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, aspartinate, glutamate, and the like; and combinations comprising one or more of the foregoing salts.

Solid dosage forms of metaxalone comprise up to about 3600 mg metaxalone, specifically about 50 to about 3200 mg metaxalone, more specifically about 100 to about 800 mg metaxalone. In one embodiment, the solid dosage form is an oral dosage form, for example, a tablet.

A "substance" taken or administered with metaxalone means a substance that affects the safety, bioavailability, plasma concentration, efficacy, or a combination comprising at least one of the foregoing of metaxalone or the substance. A "substance" can be an active agent, an herbal supplement, a nutritional supplement, a vitamin, a xenobiotic, or an environmental contaminant.

A substance is a "substrate" of enzyme activity when it can be chemically transformed by action of the enzyme on the substance. "Enzyme activity" refers broadly to the specific activity of the enzyme (i.e., the rate at which the enzyme transforms a substrate per mg or mole of enzyme) as well as the metabolic effect of such transformations. Thus, a substance is an "inhibitor" of enzyme activity when the specific activity or the metabolic effect of the specific activity of the enzyme can be decreased by the presence of the substance, without reference to the precise mechanism of such decrease. For example a substance can be an inhibitor of enzyme activity by competitive, non-competitive, allosteric or other type of enzyme inhibition, by decreasing expression of the enzyme, or other direct or indirect mechanisms. Similarly, a substance is an "inducer" of enzyme activity when the specific activity or the metabolic effect of the specific activity of the enzyme can be increased by the presence of the substance, without reference to the precise mechanism of such increase. For example a substance can be an inducer of enzyme activity by increasing reaction rate, by increasing expression of the enzyme, by allosteric activation or other direct or indirect mechanisms. It is possible for a substance to be a substrate, inhibitor, or inducer of an enzyme activity. For example, the substance can be an inhibitor of enzyme activity by one mechanism and an inducer of enzyme activity by another mechanism. The function (substrate, inhibitor, or inducer) of the substance with respect to activity of an enzyme can depend on environmental conditions.

A "user" means a patient, a medical care worker, or a pharmaceutical supplier.

The cytochrome p450 enzymes are a highly diverse superfamily of enzymes. Each cytochrome p450 enzyme is termed an "isoform" or "isozyme" since each derives from a different gene. Cytochrome p450 enzymes are categorized into families and subfamilies by amino acid sequence similarities. These enzymes are designated by the letters "CYP" followed by an Arabic numeral representing the family, a letter representing the sub-family and another Arabic numeral representing a specific gene (e.g., CYP2D6). Particular isozymes discussed herein are named as per the recommendations of the P450 Gene Superfamily Nomenclature Committee (see e.g., "P450 superfamily: Update on new sequences, gene mapping, accession numbers, and nomenclature" Pharmacogenetics 6, 1-42 1996, part A pp. 1-21.). Herein, the designation for a cytochrome p450 isozyme may encompass the homolog from any species identified as having such an isozyme. For example, CYP1A2 genes are known in at least rat, human, rabbit, hamster, dog, guinea pig, mouse and chicken and the designation "CYP1A2" includes the CYP1A2 protein from each species known to have a CYP1A2 gene. In some embodiments, the designation for a cytochrome p450 isozyme is the human isozyme.

In one embodiment, CYP1A2 is human CYP1A2 (Entrez Gene ID: 1544; reference protein sequence Genbank NP_000752), and includes any allelic variants. Specifically, CYP1A2 includes any allelic variants included in the list of human CYP1A2 allelic variants maintained by the Human Cytochrome P450 (CYP) Allele Nomenclature Committee; more specifically it includes any of the *1 through *16 alleles. Additional reference amino acid sequences for human CYP1A2 include Genbank AAK25728, AAY26399, AAA35738, AAA52163, AAA52163, AAF13599, AAH67424, AAH67425, AAH67426, AAH67427, AAH67428, AAH67429, AAA52154, AAA52146, CAA77335, P05177, Q6NWU3, Q6NWU5, Q9BXX7, and Q9UK49.

In one embodiment, CYP2A6 is human CYP2A6 (Entrez Gene ID: 1548; reference protein sequence Genbank NP_000753), and includes any CYP2A6 allelic variants. Specifically, CYP2A6 includes any allelic variants included in the list of human CYP2A6 allelic variants maintained by the Human Cytochrome P450 (CYP) Allele Nomenclature Committee; more specifically it includes any of the *1 through *22 alleles. Additional reference amino acid sequences for human CYP2A6 include Genbank AAG45229, AAB40518, AAF13600, AAH96253, AAH96254, AAH96255, AAH96256, AAA52067, CAA32097, CAA32117, P11509, Q13120, and Q4VAU0.

In one embodiment, CYP2B6 is human CYP2B6 (Entrez Gene ID: 1555; reference protein sequence Genbank NP_000758), and includes any CYP2B6 allelic variants. Specifically, CYP2B6 includes any allelic variants included in the list of human CYP2B6 allelic variants maintained by the Human Cytochrome P450 (CYP) Allele Nomenclature Committee; more specifically it includes any of the *1 through *25 alleles. Additional reference amino acid sequences for human CYP2B6 include Genbank AAF32444, AAD25924, ABB84469, AAF13602, AAH67430, AAH67431, AAA52144, P20813, Q6NWU1, Q6NWU2, and Q9UNX8.

In one embodiment, CYP2C8 is human CYP2C8 (Entrez Gene ID: 1558; reference protein sequence Genbank NP_110518), and includes any CYP2C8 allelic variants. Specifically, CYP2B8 includes any allelic variants included in the list of human CYP2C8 allelic variants maintained by the Human Cytochrome P450 (CYP) Allele Nomenclature Committee; more specifically it includes any of the *1 through *10 alleles. Additional reference amino acid sequences for human CYP2C8 include Genbank CAH71307, AAR89907, CAA38578, AAH20596, AAA35739, AAA35740, AAA52160, AAA52161, CAA35915, CAA68550, P10632, Q5VX93, Q8WWB1, and Q9UCZ9.

In one embodiment, CYP2C9 is human CYP2C9 (Entrez Gene ID: 1559; reference protein sequence Genbank NP_000762), and includes any CYP2C9 allelic variants. Specifically, CYP2CP includes any allelic variants included in the list of human CYP2C9 allelic variants maintained by the Human Cytochrome P450 (CYP) Allele Nomenclature Committee; more specifically it includes any of the *1 through *24 alleles. Additional reference amino acid sequences for human CYP2C9 include Genbank CAH71303, AAP88931, AAT94065, AAW83816, AAD13466, AAD13467, AAH20754, AAH70317, BAA00123, AAA52159, AAB23864, P11712, Q5EDC5, Q5VX92, Q6IRV8, Q8WW80, Q9UEH3, and Q9UQ59.

In one embodiment, CYP2C19 is human CYP2C19 (Entrez Gene ID: 1557; reference protein sequence Genbank NP_000760), and includes any CYP2C19 allelic variants. Specifically, CYP2C19 includes any allelic variants included in the list of human CYP2C19 allelic variants maintained by the Human Cytochrome P450 (CYP) Allele Nomenclature Committee; more specifically it includes any of the *1 through *21 alleles. Additional reference amino acid sequences for human CYP2C19 include Genbank BAD02827, CAH73444, CAH74068, AAV41877, AAL31347, AAL31348, AAA36660, AAB59426, CAA46778, P33261, Q16743, Q767A3, Q8WZB1, and Q8WZB2.

In one embodiment, CYP2D6 is human CYP2D6 (Entrez Gene ID: 1565; reference protein sequence Genbank NP_000097), and includes any CYP2D6 allelic variants. Specifically, it CYP2D6 includes any allelic variants included in the list of human CYP2D6 allelic variants maintained by the Human Cytochrome P450 (CYP) Allele Nomenclature Committee; more specifically it includes any of the *1 through *58 alleles. Additional reference amino acid sequences for human CYP2D6 include Genbank AAS55001, ABB01370, ABB01371, ABB01372, ABB01373, AAA35737, AAA53500, BAD92729, AAU87043, AAH66877, AAH67432, AAH75023, AAH75024, AAI06758, AAI06759, CAG30316, AAA52153, AAA36403, CAA30807, and P10635.

In one embodiment, CYP2E1 is human CYP2E1 (Entrez Gene ID: 1571; reference protein sequence Genbank NP_000764), and includes any CYP2E1 allelic variants. Specifically, CYP2E1 includes any allelic variants included in the list of human CYP2E1 allelic variants maintained by the Human Cytochrome P450 (CYP) Allele Nomenclature Committee; more specifically it includes any of the *1 through *7 alleles. Additional reference amino acid sequences for human CYP2E1 include Genbank CAH70047, BAA00902, BAA08796, AAA52155, AAD13753, AAF13601, CAI47002, AAH67433, AAH67435, AAZ77710, AAA35743, AAD14267, P05181, Q16868, Q5VZD5, Q6LER5, Q6NWT7, and Q6NWT9.

In one embodiment, CYP3A4 is human CYP3A4 (Entrez Gene ID: 1576; reference protein sequence Genbank NP_059488), and includes any CYP3A4 allelic variants. Specifically, CYP3A4 includes any allelic variants included in the list of human CYP3A4 allelic variants maintained by the Human Cytochrome P450 (CYP) Allele Nomenclature Committee; more specifically it includes any of the *1 through *20 alleles. Additional reference amino acid sequences for human CYP3A4 include Genbank AAF21034, AAG32290, AAG53948, EAL23866, AAF13598, CAD91343, CAD91645, CAD91345, AAH69418, AAI01632, BAA00001, AAA35747, AAA35742, AAA35744, AAA35745, CAA30944, P05184, P08684, Q6GRK0, Q7Z448, Q86SK2, Q86SK3, and Q9BZM0.

The ability of metaxalone to act as a substrate, inhibitor, or inducer of various cytochrome p450 isozymes was determined in studies described below. A summary of the findings of the studies is provided in Table 1.

TABLE 1

Summary of metaxalone effects on cytochrome p450 isozymes.

| CYP isozyme | Substrate | Inhibitor | Inducer/Inhibitor |
|---|---|---|---|
| 1A2 | + | + | + |
| 2A6 | 0 | 0 | 0 |
| 2B6 | ND | + | 0 |
| 2C8 | ND | 0 | ND |
| 2C9 | 0 | 0 | – |
| 2C19 | + | + | 0 |
| 2D6 | 0 | + | – |
| 2E1 | 0 | + | 0 |
| 3A4 | 0 | + | + |

For each possible function of metaxalone (i.e., substrate, inhibitor, or inducer), there is a column in the table. A "+" in a particular column and row indicates that the study found that metaxalone functioned in that capacity with respect to the cytochrome p450 isozyme represented in that row, while a "0" indicates that the results did not support that metaxalone functioned in that capacity with respect to the cytochrome p450 isozyme represented in that row. In the column labeled Inducer/Inhibitor, a "+" denotes that the metaxalone functioned as an inducer of the CYP isozyme, while a "–" denotes that metaxalone functioned as an inhibitor of the CYP isozyme. For example, metaxalone was found to be a substrate, inhibitor, and inducer of CYP1A2 activity, and was found to be an inhibitor of CYP2C9 activity. The symbol "ND" indicates that no experiment was performed.

As summarized in Table 1, metaxalone was found to be a substrate for CYP2C19 and CYP1A2, and therefore can also act as a competitor of other substrates for these two isozymes. Additionally, metaxalone was determined to be an inhibitor of the cytochrome p450 isozymes CYP1A2, CYP2B6, CYP2C9, CYP2C19, CYP2D6, CYP2E1, and CYP3A4 and an inducer of CYP1A2 and CYP3A4.

Enzymes involved in Phase I and Phase II active agent metabolism, such as the cytochrome p450 isozymes, respond to the constantly changing types and amounts of substrate active agents they encounter. For example, changes in active agent metabolism due to competition for the same cytochrome p450 isoform can change the clinical effectiveness or safety of an active agent by altering the plasma concentration of the active agent or its metabolite(s). Similarly, inhibition or induction of the cytochrome p450 isoform that metabolizes a particular active agent can change the clinical effectiveness or safety of that active agent. Therefore, for any cytochrome p450 for which metaxalone acts as a substrate, inhibitor, or inducer, the administration of metaxalone with a substance that is a substrate, inhibitor, or inducer of that cytochrome p450 can affect the metabolism of the metaxalone or the substance. For the case in which the substance is a narrow therapeutic index active agent, such as warfarin or phenytoin, too little of the active agent in the blood stream can lead to insufficient therapeutic activity, while a too large dose of the active agent can lead to excessive therapeutic activity or toxicity, both of which can be detrimental.

The invention provides methods of using metaxalone. These methods include using metaxalone in the treatment of various diseases or conditions, including, for example, musculoskeletal conditions, specifically acute and painful musculoskeletal conditions, muscle sprains, muscle spasms, spasticity, low back pain and stiffness, acute lumbosacral pain, cervical stiffness or torticohis; as well as head pain, including migraines, cluster headaches, tension headaches, or tension related migraines.

In one embodiment, the method comprises informing a user that metaxalone affects activity of a cytochrome p450 isozyme. The cytochrome p450 isozyme may be any cytochrome p450 isozyme. For example the cytochrome p450 isozyme may be CYP1A2 CYP2B6, CYP2C9, CYP2C19, CYP2D6, CYP2E1, or CYP3A4. In some embodiments the cytochrome p450 isozyme is CYP1A2, CYP3A4, or CYP2C19. In certain embodiments the cytochrome p450 isozyme is a human enzyme. In some embodiments, the method further comprises providing the user with metaxalone.

Informing the user that metaxalone affects the activity of a cytochrome p450 isozyme includes providing a user with information about any effect of metaxalone on the activity of any cytochrome p450 isozyme. Informing the user that metaxalone affects the activity of a cytochrome p450 isozyme includes informing a user of any of the following: that metaxalone is metabolized by a cytochrome p450 isozyme; that metaxalone is an inducer of activity of a cytochrome p450 isozyme; that a cytochrome p450 isozyme metabolizing metaxalone is CYP1A2 or CYP2C19; that metaxalone is a competitive inhibitor of CYP1A2 or CYP2C19; that metaxalone is a substrate of CYP1A2 or CYP2C19; that there is a potential active agent interaction between metaxalone and an active agent that is a substrate, inhibitor, or inducer of CYP1A2 or CYP2C19; that metaxalone is an inhibitor of a cytochrome p450 isozyme; that caution is recommended when metaxalone and a substrate of CYP2B6, CYP2C9, CYP2C19, or CYP2D6 are administered to a patient known to have a poor metabolizer phenotype for or that has reduced activity of CYP2B6, CYP2C9, CYP2C19, or CYP2D6; that caution is recommended when administering metaxalone with the substance when the substance is an active agent having a narrow therapeutic index; that the allelic variants of CYP2B6, CYP2C9, CYP2C19, or CYP2D6 present in the patient can further affect the potential active agent interaction between metaxalone and an active agent; that there is a potential active agent interaction of metaxalone with an active agent that is a substrate of the cytochrome p450 isozyme; that there is a potential active agent interaction of metaxalone with warfarin; that metaxalone affects the activity of CYP1A2, CYP2B6, CYP2C9, CYP2C19, CYP2D6, CYP2E1, or CYP3A4; that there is a potential active agent interaction of metaxalone with a substance that is a substrate of CYP1A2, CYP2B6, CYP2C9, CYP2C19, CYP2D6, CYP2E1, or CYP3A4; that metaxalone is an inhibitor of CYP1A2, CYP2B6, CYP2C9, CYP2C19, CYP2D6, CYP2E1, or CYP3A4; and that metaxalone is an inducer of CYP1A2 or CYP3A4 activity; that there is a potential active agent interaction of metaxalone with a substance that is a substrate of CYP1A2 or CYP3A4.

The method can further comprise informing the user that administration of metaxalone with a substance can affect the plasma concentration, bioavailability, safety, efficacy, or a combination comprising at least one of the foregoing of metaxalone or the substance. In some embodiments, the method further comprises providing the user with the substance.

The effect of coadministration of metaxalone and the substance can be determined by comparison of the plasma concentration, bioavailability, safety, efficacy, or a combination comprising at least one of the foregoing of the substance with and without coadministration of metaxalone or by comparison of the plasma concentration, bioavailability, safety, efficacy, or a combination comprising at least one of the foregoing of metaxalone with and without coadministration of the substance.

Informing the user that administration of metaxalone with a substance can affect the plasma concentration, bioavailability, safety, efficacy, or a combination comprising at least one of the foregoing of metaxalone or the substance includes providing a user with information about any effect of metaxalone on plasma concentration, bioavailability, safety, efficacy, or a combination comprising at least one of the foregoing of metaxalone or the substance. This includes informing a user of any of the following: that taking metaxalone with an active agent can affect the bioavailability, safety, or efficacy of the active agent or metaxalone; that administration of metaxalone and a substance that is a substrate, inhibitor, or inducer of CYP1A2 or CYP2C19 can affect plasma concentration, bioavailability, safety, efficacy, or a combination comprising at least one of the foregoing of metaxalone or the substance; that administration of metaxalone with a substance that is a CYP1A2 or CYP2C19 substrate can increase the plasma concentration of the substance; that taking metaxalone with an active agent that is a substrate, inhibitor, or inducer of CYP1A2 or CYP2C19 can affect the plasma concentration, bioavailability, safety, efficacy, or a combination comprising at least one of the foregoing of metaxalone or the active agent; that administration of metaxalone with an active agent that is a cytochrome p450 isozyme substrate having a narrow therapeutic index can affect plasma concentration, bioavailability, safety, efficacy, or a combination comprising at least one of the foregoing of the active agent; that administration of metaxalone with an active agent that is a CYP1A2 or CYP2C19 substrate having a narrow therapeutic index can affect plasma concentration, bioavailability, safety, efficacy, or a combination comprising at least one of the foregoing of the active agent; that metaxalone can affect the plasma concentration, bioavailability, safety, efficacy, or a combination comprising at least one of the foregoing of an active agent that is a substrate of the cytochrome p450 isozyme; that administration of metaxalone with an active agent that is a substrate of the cytochrome p450 isozyme and that has a narrow therapeutic index can increase plasma concentration of the active agent; that a substance that induces CYP1A2 or CYP2C19 activity can decrease metaxalone plasma concentration; that a substance that inhibits CYP1A2 or CYP2C19 activity can increase metaxalone plasma concentration; that a substance that is a substrate of CYP1A2 or CYP2C19 can increase plasma concentration of metaxalone or the substance; that administration of metaxalone with warfarin can affect the plasma concentration, bioavailability, safety, efficacy, or a combination comprising at least one of the foregoing of metaxalone or warfarin; that administration of metaxalone with an active agent that is a known substrate, inhibitor, or inducer of CYP1A2 or CYP2C19 or that is a substrate of CYP2B6, CYP2C9, CYP2D6, CYP2E1, or CYP3A4 metaxalone can affect plasma concentration, bioavailability, safety, efficacy, or a combination comprising at least one of the foregoing of the active agent or metaxalone; that the plasma concentration of a substance that is a substrate of CYP1A2, CYP2B6, CYP2C9, CYP2C19, CYP2D6, CYP2E1, or CYP3A4 can decrease when the substance is administered with metaxalone; that administration of metaxalone with a substance that is a substrate of CYP1A2, CYP2B6, CYP2C9, CYP2C19, CYP2D6, CYP2E1, or CYP3A4 can affect plasma concentration, bioavailability, safety, efficacy, or a combination comprising at least one of the foregoing of the substance; that administration of metaxalone with an active agent that is a CYP1A2, CYP2B6, CYP2C9, CYP2C19, CYP2D6, CYP2E1, or CYP3A4 substrate having a narrow therapeutic index can affect plasma concentration, bioavailability, safety, efficacy, or a combination comprising at least one of the foregoing of the active agent; that the plasma concentration of a substance that is a substrate of CYP1A2 or CYP3A4 can decrease when the substance is administered with metaxalone; that administration of metaxalone and a substance that is a substrate of CYP1A2 or CYP3A4 activity can affect plasma concentration, bioavailability, safety, efficacy, or a combination comprising at least one of the foregoing of the substance.

In another embodiment, the method comprises informing a user that metaxalone is metabolized by a cytochrome p450 isozyme. The cytochrome p450 isozyme metabolizing metaxalone is CYP1A2 or CYP2C19. In some embodiments, the method further comprises informing the user that administration of metaxalone and a substance that is a substrate, inhibitor, or inducer of CYP1A2 or CYP2C19 can affect plasma concentration, bioavailability, safety, efficacy, or a combination comprising at least one of the foregoing of metaxalone or the substance. Methods provided herein include informing a user that the substance or metaxalone is a substrate, inhibitor, or inducer of CYP1A2 or CYP2C19. The substance can inhibit CYP1A2 or CYP2C19 activity and the effect can be an increase in metaxalone plasma concentration, or the substance can induce CYP1A2 or CYP2C19 activity and the effect can be a decrease in metaxalone plasma concentration. In yet another embodiment, the user is informed that the substance is a substrate of CYP1A2 or CYP2C19 and plasma concentration of the substance or metaxalone can increase. In yet another embodiment, the method comprises informing the user that taking metaxalone and a substance that is a substrate of CYP1A2 or CYP2C19 can increase plasma concentration of metaxalone or the substance.

The method also comprises informing a user that metaxalone is an inhibitor or an inducer of a cytochrome p450 isozyme. Cytochrome p450 isozymes inhibited by metaxalone include CYP1A2, CYP2B6, CYP2C9, CYP2C19, CYP2D6, CYP2E1, and CYP3A4. Cytochrome p450 isozymes that are induced by metaxalone include CYP1A2 and CYP3A4. In some embodiments the method further comprises informing a user that administration of metaxalone and a substance that is a substrate of the cytochrome p450 isozyme can affect plasma concentration, bioavailability, safety, efficacy, or a combination comprising at least one of the foregoing of the substance. In some embodiments, the method can further comprise informing that metaxalone is an inhibitor of the cytochrome p450 isozyme or that the effect on the substance can be an increase in plasma concentration. In other embodiments, the method can further comprise informing that metaxalone is an inducer of CYP1A2 or CYP3A4 or that the effect on the substance can be a decrease in plasma concentration.

In some embodiments, the method can further comprise providing the user with metaxalone. Other embodiments include administering metaxalone or another substance. Administration may be to a patient by the patient, a medical worker, or other user. Metaxalone can be administered in a therapeutically effective amount. In some embodiments, the method can further comprise providing the user with metaxalone or informing the user that caution is recommended when administering metaxalone with the substance when the substance is an active agent having a narrow therapeutic index.

The information provided to a user can comprise any combination of information disclosed herein concerning the effects of metaxalone on the activity of a cytochrome p450 isozyme or on the plasma concentration, bioavailability, safety, efficacy, or a combination comprising at least one of the foregoing of metaxalone or a substance. The information may also comprise any combination of information disclosed herein concerning the effects of a substance on the activity of a cytochrome p450 isozyme or on the plasma concentration, bioavailability, safety, efficacy, or a combination comprising at least one of the foregoing of metaxalone or a substance when the substance is used with metaxalone.

Medical information provided in any of the methods described herein concerning the effects of administering metaxalone with an additional substance may alternatively be provided in layman's terms, so as to be better understood by patients or non-medical professionals. Those of skill in the medical art are familiar with the various layman's terms that can be used to describe the effects of active agent interactions.

In yet another embodiment, the method of using metaxalone comprises obtaining metaxalone from a container providing information that metaxalone affects activity of a cytochrome p450. Information can also be provided that administering metaxalone with a substance can affect plasma concentration, bioavailability, safety, efficacy, or a combination comprising at least one of the foregoing of the substance or metaxalone. The method also comprises providing metaxalone in the container providing such information. The method may also comprise providing a substance, such as an active agent, in a container providing information that metaxalone affects activity of a cytochrome p450 or that administering metaxalone with the substance may affect plasma concentration, bioavailability, safety, efficacy, or a combination comprising at least one of the foregoing of the substance or metaxalone. The provided information may be any information disclosed herein concerning the effects of metaxalone or a substance on the activity of a cytochrome p450 isozyme or any information disclosed herein concerning the effects of metaxalone when administered with a substance on the plasma concentration, bioavailability, safety, efficacy, or a combination comprising at least one of the foregoing of the substance or metaxalone. The method can further comprise ingesting the metaxalone or the substance.

The method of use can further comprise monitoring a patient's plasma concentration of an active agent as $AUC_{0-INF}$, $AUC_{0-t}$, $C_{MAX}$, or a combination of any of the foregoing pharmacokinetic parameters.

The method may also comprise informing the user or providing information that, when an active agent and metaxalone are administered to a patient, that it is recommended that a medical care worker determine the patient's plasma concentration of the active agent; and alter dosing of the active agent for the patient based on the determined active agent plasma concentration. Additionally, the method can comprise determining the metabolizer phenotype of the patient or the allelic variant of the patient for a cytochrome p450 isozyme; specifically the cytochrome p450 isozyme is CYP2B6, CYP2C9, CYP2C19, or CYP2D6.

Various laboratory methods are known, including ones that are commercially available, for detecting the presence of allelic variants of cytochrome p450 isozymes in an individual or determining the metabolizer phenotype of an individual for a particular cytochrome p450 isozyme. Any suitable method known in the art may be used. Methods include analyzing a blood sample from the individual to determine the allelic variant of a particular cytochrome p450 isozyme gene present in the individual (for example by genotyping or haplotyping DNA or RNA from the gene using mass spectrometry, gel electrophoresis, or TAQMAN assays; or analyzing the protein sequence expressed by the gene). The metabolizer phenotype of the individual can be inferred based on the known properties of the allelic variants determined to be present in the individual. Alternatively, the blood sample can be used to measure enzyme activity of the cytochrome p450 isozyme using a suitable assay amd isozyme-selective substrate. Among suitable isozyme-selective substrates are those used in the studies herein, or those suggested in FDA guidelines directed to collecting cytochrome p450 isozyme data for regulatory submissions relating to an active agent.

Food may alter the release of an active agent from a dosage form, the solubilization of the active agent, and the transport of the active agent across the intestinal wall. According to U.S. Pat. No 6,407,128, pharmacokinetic studies of metaxalone indicate that food increases the rate and extent of absorption of a 400 mg oral dosage form in humans. In that study, food increased peak plasma concentrations ($C_{max}$), and extent of absorption ($AUC_{0-t}$, $AUC_{0-inf}$) relative to a fasted treatment with observed increases of 177.5%, 123.5%, and 115.4%. Based on that study, administration of metaxalone with food increases the bioavailability of metaxalone and therefore a particular oral dose given with food may physiologically correspond to a higher plasma concentration of metaxalone than the same oral dose given in a fasted state. Consequently, any effect on plasma concentration, bioavailability, safety, efficacy, or a combination comprising at least one of the foregoing of administration of metaxalone with an additional substance which is a substrate, inhibitor, or inducer of a cytochrome p450 isozyme for which metaxalone is a substrate, inhibitor, or inducer can be further affected by whether or not the metaxalone was administered with food.

Methods of using metaxalone comprise informing a user that metaxalone affects the activity of a cytochrome p450; that administration of metaxalone with a substance can affect the plasma concentration, bioavailability, safety, efficacy, or a combination comprising at least one of the foregoing of metaxalone or the substance; and that any effect on the plasma concentration, bioavailability, safety, efficacy, or a combination comprising at least one of the foregoing of metaxalone or the substance can vary with administration of metaxalone with or without food.

In another embodiment, the method of using metaxalone comprises obtaining metaxalone from a container providing information that metaxalone affects activity of a cytochrome p450; that administration of metaxalone with a substance can affect the plasma concentration, bioavailability, safety, or efficacy of metaxalone or the substance; and that any effect on the plasma concentration, bioavailability, safety, or efficacy of metaxalone or the substance can vary with administration of metaxalone with or without food. The method also includes providing metaxalone in the container providing information.

In one embodiment, the metaxalone is always administered with food. In another embodiment, the metaxalone is always administered without food. In yet another embodiment, the metaxalone is sometimes administered with food and sometimes administered without food.

Also disclosed herein are methods of manufacturing a metaxalone pharmaceutical product.

In one embodiment, the method comprises packaging a metaxalone dosage form with information that metaxalone affects activity of a cytochrome p450 isozyme. The information may also advise that administration of metaxalone with a substance can affect the plasma concentration, bioavailability, safety, efficacy, or a combination comprising at least one of the foregoing of metaxalone or the substance. The information may also include any information disclosed herein about the effect of metaxalone or a substance on the activity of a cytochrome p450 isozyme and any information disclosed herein about the effect of metaxalone or a substance on the plasma concentration, bioavailability, safety, efficacy, or a combination comprising at least one of the foregoing of metaxalone or the substance.

In an embodiment, the method comprises packaging a metaxalone dosage form with information that metaxalone is metabolized by a cytochrome p450 isozyme. The cytochrome p450 isozyme metabolizing metaxalone is CYP1A2 or CYP2C19. The information may also advise that administration of metaxalone and a substance that is a substrate, inhibitor, or inducer of CYP1A2 or CYP2C19 can affect plasma concentration, bioavailability, safety, efficacy, or a combination comprising at least one of the foregoing of metaxalone or the substance.

In an embodiment, the method comprises packaging a metaxalone dosage form with information that administration of metaxalone with an active agent that is a CYP1A2 or CYP2C19 substrate having a narrow therapeutic index can affect plasma concentration, bioavailability, safety, efficacy, or a combination comprising at least one of the foregoing of the active agent.

In another embodiment, the method comprises packaging a metaxalone dosage form with information that metaxalone is an inhibitor or an inducer of a cytochrome p450 isozyme. The information may further advise that administration of metaxalone with an active agent that is a substrate of the cytochrome p450 isozyme can affect the plasma concentration, bioavailability, safety, efficacy, or a combination comprising at least one of the foregoing of the active agent. The cytochrome p450 isozyme is CYP1A2, CYP2B6, CYP2C9, CYP2C19, CYP2D6, CYP2E1, or CYP3A4. In some embodiments, the active agent is a substrate of the cytochrome p450 isozyme inhibited by metaxalone and the plasma concentration of the active agent can increase; in other embodiments, the active agent is a substrate of the cytochrome p450 isozyme induced by metaxalone and the plasma concentration of the active agent can decrease.

In yet another embodiment, the method comprises packaging a metaxalone dosage form with information that metaxalone affects activity of a cytochrome p450 isozyme and that administration of metaxalone with a substance can affect the plasma concentration, bioavailability, safety, efficacy, or a combination comprising at least one of the foregoing of the metaxalone or the substance; and that any effect on the plasma concentration, bioavailability, safety, efficacy, or a combination comprising at least one of the foregoing of metaxalone or the substance can vary with administration of metaxalone with or without food. In one embodiment, the metaxalone is always administered with food. In another embodiment, the metaxalone is always administered without food. In yet another embodiment, the metaxalone is sometimes administered with food and sometimes administered without food.

Another aspect of the invention is a method of using an active agent that is a known substrate, inhibitor, or inducer of CYP1A2 or CYP2C19 or that is a substrate of a cytochrome p450 isozyme.

In one embodiment, the method comprises informing a user that metaxalone affects activity of a cytochrome p450 isozyme and that administration of the active agent and metaxalone can affect the plasma concentration, bioavailability, safety, efficacy, or a combination comprising at least one of the foregoing of the active agent or the metaxalone. The cytochrome p450 isozyme is CYP1A2, CYP2B6, CYP2C9, CYP2C19, CYP2D6, CYP2E1, or CYP3A4. In some embodiments, the method further comprises providing the user with the active agent or metaxalone.

In another embodiment, the method comprises obtaining an active agent that is a known substrate, inhibitor, or inducer of CYP1A2 or CYP2C19 or that is a substrate of a cytochrome p450 isozyme from a container providing information that metaxalone affects activity of a cytochrome p450 isozyme and that the administration of the active agent with metaxalone can affect plasma concentration, bioavailability, safety, efficacy, or a combination comprising at least one of the foregoing of the active agent or the metaxalone. The method may also comprise providing the active agent in the container providing information.

Also disclosed herein is a method of manufacturing a pharmaceutical product of an active agent that is a known substrate, inhibitor, or inducer of CYP1A2 or CYP2C19 or that is a substrate of a cytochrome p450 isozyme.

In one embodiment, the method comprises packaging a dosage form of an active agent that is a known substrate, inhibitor, or inducer of CYP1A2 or CYP2C19 or that is a substrate of a cytochrome p450 isozyme with information that metaxalone affects activity of a cytochrome p450 isozyme.

In each of the methods for using an active agent that is a known substrate, inhibitor, or inducer of CYP1A2 or CYP2C19 or that is a substrate of a cytochrome p450 isozyme or the methods of manufacturing a pharmaceutical product of such an active agent, the information provided to the user or with the dosage form may include any information disclosed herein about the effect of metaxalone or the active agent on the activity of a cytochrome p450 isozyme and any information disclosed herein about the effect of metaxalone or the active agent on the plasma concentration, bioavailability, safety, efficacy, or a combination comprising at least one of the foregoing of metaxalone or the active agent.

The invention provides articles of manufacture.

In some embodiments, the article of manufacture comprises a container containing a dosage form of metaxalone.

In one embodiment, the container is associated with published material informing that metaxalone affects activity of a cytochrome p450 isozyme. The published material can further inform that administration of metaxalone with a substance that is a substrate, inhibitor, or inducer of the cytochrome p450 isozyme can affect plasma concentration, bioavailability, safety, efficacy, or a combination comprising at least one of the foregoing of metaxalone or the substance.

The published material may be in the form of printed labeling, or in some other form. The cytochrome p450 can be CYP1A2, CYP2B6, CYP2C9, CYP2C19, CYP2D6, CYP2E1, or CYP3A4. The published material comprising the article of manufacture may also include any information disclosed herein about the effect of metaxalone or a substance on the activity of a cytochrome p450 isozyme and any information disclosed herein about the effect of metaxalone or a substance on the plasma concentration, bioavailability, safety, efficacy, or a combination comprising at least one of the foregoing of metaxalone or the substance.

In another embodiment, the container is associated with published material informing that metaxalone is metabolized by a cytochrome p450 isozyme. The cytochrome p450 isozyme metabolizing metaxalone is CYP1A2 or CYP2C19. In some embodiments, the published material further informs that administration of metaxalone with a substance that is a substrate, inhibitor, or inducer of CYP1A2 or CYP2C19 can affect plasma concentration, bioavailability, safety, efficacy, or a combination comprising at least one of the foregoing of metaxalone or the substance. In other embodiments, the published material further informs that a substance that induces CYP1A2 or CYP2C19 activity can decrease metaxalone plasma concentration, that a substance that inhibits CYP1A2 or CYP2C19 activity can increase metaxalone plasma concentration, or that a substance that is a substrate of CYP1A2 or CYP2C19 can increase plasma concentration of metaxalone or the substance.

In yet another embodiment, the container is associated with published material informing that metaxalone is an inhibitor or an inducer of a cytochrome p450 isozyme. The published material may further inform that administration of metaxalone can affect the plasma concentration, bioavailability, safety, efficacy, or a combination comprising at least one of the foregoing of substances that are substrates of the cytochrome p450 isozyme. The cytochrome p450 isozyme is CYP1A2, CYP2B6, CYP2C9, CYP2C19, CYP2D6, CYP2E1, or CYP3A4.

In another embodiment, the container is associated with published material that includes information that caution is recommended when administering metaxalone with the substrate, wherein the substrate has a narrow therapeutic index.

In yet another embodiment, the container is associated with published material informing that metaxalone affects activity of a cytochrome p450 isozyme; that administration to a patient of metaxalone with a substance can affect plasma concentration, bioavailability, safety, efficacy, or a combination comprising at least one of the foregoing of metaxalone or the substance; and that any effect on the plasma concentration, bioavailability, safety, efficacy, or a combination comprising at least one of the foregoing of metaxalone or the substance can vary with administration of metaxalone with or without food.

In yet another embodiment, the article comprises a container comprising a dosage form of metaxalone, and published material. In one embodiment, the published material provides information that there is a potential active agent interaction with warfarin; or that administration with warfarin can affect the bioavailability, safety, or efficacy of metaxalone or warfarin. In another embodiment, the published material informs that metaxalone affects activity of CYP1A2, CYP2B6, CYP2C9, CYP2C19, CYP2D6, CYP2E1, or CYP3A4. The published material may further inform that there is a potential active agent interaction with a substance that is a substrate of CYP1A2, CYP2B6, CYP2C9, CYP2C19, CYP2D6, CYP2E1, or CYP3A4 or that administration of metaxalone with a substance that is a substrate of CYP1A2, CYP2B6, CYP2C9, CYP2C19, CYP2D6, CYP2E1, or CYP3A4 can affect plasma concentration, bioavailability, safety, efficacy, or a combination comprising at least one of the foregoing of the substance. In another embodiment, the published material informs that metaxalone is a substrate of CYP1A2 or CYP2C19. The published material may also inform that there is a potential active agent interaction with a substance that is a substrate, inhibitor, or inducer of CYP1A2 or CYP2C19 or that administration of metaxalone with a substance that is a substrate, inhibitor, or inducer of CYP1A2 or CYP2C19 can affect plasma concentration, bioavailability, safety, efficacy, or a combination comprising at least one of the foregoing of metaxalone or the substance. In yet another embodiment, the published material informs that metaxalone is an inhibitor of activity of CYP1A2, CYP2B6, CYP2C9, CYP2C19, CYP2D6, CYP2E1, or CYP3A4. In yet another embodiment, the published material informs that metaxalone is an inducer of activity of CYP1A2 or CYP3A4. In each of these latter embodiments, the published material may further inform that there is a potential active agent interaction with a substance that is a substrate of CYP1A2, CYP2B6, CYP2C9, CYP2C19, CYP2D6, CYP2E1, or CYP3A4 or that administration of metaxalone with a substance that is a substrate of CYP1A2, CYP2B6, CYP2C9, CYP2C19, CYP2D6, CYP2E1, or CYP3A4 can affect plasma concentration, bioavailability, safety, efficacy, or a combination comprising at least one of the foregoing of the substance. In some embodiments, the published material can be printed labeling.

Also disclosed herein is an article of manufacture comprising packaging material and a dosage form contained within the packaging material, wherein the dosage form comprises, as at least one active ingredient, metaxalone, and wherein the packaging material comprises a label approved by a regulatory agency for the product. The label may inform that metaxalone affects activity of a cytochrome p450 isozyme; that a cytochrome p450 isozyme metabolizing metaxalone is CYP1A2 or CYP2C19; that metaxalone is an inhibitor of activity of CYP1A2, CYP2B6, CYP2C9, CYP2C19, CYP2D6, CYP2E1, or CYP3A4; or that metaxalone is an inducer of activity of CYP1A2 or CYP3A4. Examples of regulatory agencies are the US FDA or the European Agency for the Evaluation of Medicinal Products (EMEA).

The invention further includes an article of manufacture comprising a container holding a dosage form of metaxalone associated with published material informing that there is a potential active agent interaction with warfarin, or that administration with warfarin can affect the bioavailability, safety, or efficacy of the metaxalone or the warfarin. The published material may further comprise instructions regarding measuring the Prothrombin Time/International Normalized Ratio daily, every other day, weekly, every other week, monthly, or according to another schedule or time criteria, or instructions to monitor the blood levels of warfarin as $AUC_{0-t}$, $AUC_{0-INF}$, $C_{MAX}$, or a combination comprising one or more of the foregoing pharmacokinetic parameters.

The invention includes articles of manufacture in which the substance administered with metaxalone is phenytoin. In one embodiment, the article of manufacture comprises a container holding a dosage form of metaxalone associated with published material informing that there is a potential active agent interaction with phenytoin, or that administration of metaxalone with phenytoin can affect the bioavailability, safety, efficacy or a combination comprising at least one of the foregoing of the metaxalone or the phenytoin. The published material may further comprise instructions to monitor the blood levels of phenytoin as $AUC_{0-t}$, $AUC_{0-INF}$, $C_{MAX}$, or a combination comprising one or more of the foregoing pharmacokinetic parameters.

Also disclosed herein is an article of manufacture comprising a container containing a dosage form of an active agent that is a known substrate, inhibitor, or inducer of CYP1A2 or CYP2C19 or that is a substrate of a cytochrome p450 isozyme. The container is associated with published material informing that metaxalone affects activity of a cytochrome p450 isozyme and administration to a patient of the active agent and metaxalone can affect plasma concentration, bioavailability, safety, efficacy, or a combination comprising at least one of the foregoing of the active agent or metaxalone. In one embodiment of any of these methods or articles involving an active agent that is a known substrate, inhibitor or inducer of CYP1A2 or CYP2C19 or that is a substrate of a cytochrome p450 isozyme, the active agent is an inducer of CYP1A2 or CYP2C19 and plasma concentration of metaxalone can decrease. In another embodiment the active agent is an inhibitor of CYP1A2 or CYP2C19 and plasma concentration of metaxalone can increase. In yet another embodiment, the active agent is a substrate of CYP1A2 or CYP2C19 and plasma concentration of the active agent and/or metaxalone can increase. In yet another embodiment, the active agent is a substrate of CYP1A2, CYP2B6, CYP2C9, CYP2C19, CYP2D6, CYP2E1, or CYP3A4 and plasma concentration of the active agent can increase. In yet another embodiment, the active agent is a substrate of CYP1A2 or CYP3A4 and plasma concentration of the active agent can decrease. In any of these embodiments, the active agent can have a narrow therapeutic index. The published material comprising the article of manufacture may also include any information disclosed herein about the effect of metaxalone or the active agent on the activity of a cytochrome p450 isozyme and any information disclosed herein about the effect of metaxalone or the active agent on the plasma concentration, bioavailability, safety, efficacy, or a combination comprising at least one of the foregoing of metaxalone or the active agent.

In embodiments of the articles of manufacture, the dosage form will typically be contained in a suitable container capable of holding and dispensing the dosage form and which will not significantly interact with the active agent(s) in the dosage form. Further, the container will be in physical relation with the published material. The published material may be associated with the container by any means that maintains physical proximity of the two. By way of example, the container and the published material can both be contained in a packaging material such as a box or plastic shrink wrap. Alternatively, the published material can be bonded to the container, such as with glue that does not obscure the published material, or with other bonding or holding means. Yet another alternative is that the published material is placed within the container with the dosage form.

In other embodiments of the article, someone hands the published material to the patient, for example a pharmacist can hand a product insert to a patient in conjunction with dispensing the dosage form. The published material may be a product insert, flyer, brochure, or a packaging material for the dosage form such as a bag, or the like.

In any of the embodiments disclosed herein the published material or information associated with or provided by a container can be contained in any fixed and tangible medium. For example, the information can be part of a leaflet, brochure, or other printed material provided with a container or separate from a container. The information can also take the form of a flyer, advertisement, or the label for marketing the active agent approved by a regulatory agency. The information can also be recorded on a compact disk, DVD or any other recording or electronic medium.

The substance used with metaxalone in the methods and articles of manufactures described herein may have certain effects, direct or indirect, on the activity of a cytochrome p450 enzyme. The substance or metaxalone can be a substrate, inhibitor, or inducer of a Phase I or Phase II metabolic enzyme; specifically, the substance or metaxalone is a substrate, inhibitor, or inducer of a cytochrome p450 isozyme. More specifically, the substance can be a substrate of CYP1A2, CYP2B6, CYP2C9, CYP2C19, CYP2D6, CYP2E1, or CYP3A4, or an inhibitor or inducer of CYP1A2 or CYP2C19. Metaxalone can be a substrate, inhibitor, or inducer of CYP1A2; a substrate or inhibitor of CYP2C19; an inhibitor of CYP2B6, CYP2C9, CYP2D6, or CYP2E1; or an inhibitor or inducer of CYP3A4. For example in certain embodiments the substance is: a substrate, inhibitor, or inducer of a cytochrome p450 isozyme; an active agent; a substrate, inhibitor, or inducer of CYP1A2 or CYP2C19 activity; an active agent with a narrow therapeutic index; an inducer of CYP1A2 or CYP2C19 activity and plasma concentration of metaxalone can decrease; an inhibitor of CYP1A2 or CYP2C19 and plasma concentration of metaxalone can increase; a substrate of CYP1A2 or CYP2C19 and plasma concentration of the substance or metaxalone can increase; a substrate of CYP1A2, CYP2B6, CYP2C9, CYP2C19, CYP2D6, CYP2E1, or CYP3A4 and plasma concentration of the substance can increase; or the substance is a substrate of CYP1A2 or CYP3A4 and plasma concentration of the substance can decrease when the substance is administered with metaxalone.

In any of the above methods or articles, the substance can be an active agent.

Examples of active agents that are substrates of CYP1A2 include amitriptyline, caffeine, clomipramine, clozapine, cyclobenzaprine, estradiol, fluvoxamine, haloperidol, imipramine, mexiletine, naproxen, olanzapine, ondansetron, phenacetin, acetaminophen, propranolol, riluzole, ropivacaine, tacrine, theophylline, tizanidine, verapamil, (R)-warfarin, zileuton, and zolmitriptan. Examples of active agents that are inhibitors of CYP1A2 include amiodarone, cimetidine, fluoroquinolones, fluvoxamine, furafylline, interferon, methoxsalen, and mibefradil. Examples of inducers of CYP1A2 include insulin, methyl cholanthrene, modafinil, nafcillin, beta-naphthoflavone, omeprazole, and tobacco.

Examples of active agents that are substrates of CYP2C19 include the proton pump inhibitors: lansoprazole, omeprazole, pantoprazole, and E-3810; the anti-epileptics: diazepam, phenytoin, fosphenytoin, S-mephenytoin, and phenobarbitone (Phenobarbital); as well as amitriptyline, carisoprodol, citalopram, clomipramine, cyclophosphamide, hexobarbital, imipramine, indomethacin, R-mephobarbital, moclobemide, nelfinavir, nilutamide, primidone, progesterone, proguanil, propranolol, teniposide, and R-warfarin. Examples of active agents that are inhibitors of CYP2C19 include chloramphenicol, cimetidine, felbamate, fluoxetine, fluvoxamine, indomethacin, ketoconazole, lansoprazole, modafinil, omeprazole, oxcarbazepine, probenicid, ticlopidine, and topiramate. Examples of inducers of CYP2C19 include carbamazepine, norethindrone, prednisone, and rifampin (rifampicin).

Examples of active agents that are substrates of CYP2B6 include bupropion, cyclophosphamide, efavirenz, ifosfamide, and methadone.

Examples of active agents that are substrates of CYP2C9 include diclofenac, ibuprofen, meloxicam, S-naproxen, piroxicam, suprofen, tolbutamide, glipizide, losartan, irbesartan, glyburide (glibenclamide), glipizide, glimepiride, amitriptyline, celecoxib, fluoxetine, fluvastatin, nateglinide, phenytoin, rosiglitazone, tamoxifen, torsemide, and S-warfarin.

Examples of active agents that are substrates of CYP2D6 include carvedilol, S-metoprolol, propafenone, timolol; amitriptyline, clomipramine, desipramine, imipramine, paroxetine; haloperidol, perphenazine, risperidone, thioridazine; alprenolol, amphetamine, aripiprazole, atomoxetine, bufuralol, chlorpheniramine, chlorpromazine, codeine, debrisoquine, dexfenfluramine, dextromethorphan, duloxetine, encainide, flecainide, fluoxetine, fluvoxamine, lidocaine, metoclopramide, methoxyamphetamine, mexiletine, minaprine, nebivolol, nortriptyline, ondansetron, perhexiline, phenacetin, phenformin, propranolol, sparteine, tamoxifen, tramadol, and venlafaxine.

Examples of substrates of CYP2E1 include enflurane, halothane, isoflurane, methoxyflurane, sevoflurane; acetaminophen, aniline, benzene, chlorzoxazone, ethanol, N,N-dimethyl formamide, and theophylline.

Examples of substrates of CYP3A4 include clarithromycin, erythromycin, telithromycin: quinidine; alprazolam, diazepam, midazolam, triazolam; cyclosporine, tacrolimus (FK506); indinavir, nelfinavir, ritonavir, saquinavir; cisapride; astemizole, chlorpheniramine, terfenadine; amlodipine, diltiazem, felodipine, lercanidipine, nifedipine, nisoldipine, nitrendipine, verapamil; atorvastatin, cerivastatin, lovastatin, simvastatin; estradiol, hydrocortisone, progesterone, testosterone; alfentanyl, aripiprazole, buspirone, cafergot, caffeine, cilostazol, cocaine, codeine, dapsone, dextromethorphan, docetaxel, domperidone, eplerenone, fentanyl, finasteride, gleevec, haloperidol, irinotecan, Levo-Alpha Acetyl Methadol (LAAM), lidocaine, methadone, nateglinide, odanestron, pimozide, propranolol, quinine, salmeterol, sildenafil, sirolimus, tamoxifen, taxol, terfenadine, trazodone, vincristine, zaleplon, and zolpidem.

In any of the embodiments described herein, the substance can be an active agent having a narrow therapeutic index. Examples of narrow therapeutic index active agents include warfarin, phenytoin, fosphenytoin, thioridazine, theophylline, cyclosporine, and pimozide.

In some embodiments, the active agent comprises warfarin. Warfarin, 3-(α-acetonylbenzyl)4-hydroxycoumarin, is an anticoagulant, which is eliminated by metabolism by cytochrome p450 isoforms including CYP2C9, CYP2C19, CYP2C8, CYP2C18, CYP1A2, and CYP3A4. Warfarin has a narrow therapeutic index such that too little can lead to excessive clotting, while excessive warfarin can lead to excessive bleeding. The dosing of warfarin is individualized according to the patient's sensitivity to the active agent as indicated, for example, by the Prothrombin Time/International Normalized Ratio (PT/INR). The PT/INR gives an indication of how fast blood is clotting. The recommended initial dose is 2-5 mg/day, with 2-10 mg/day as the maintenance dose. Warfarin tablets for oral administration include tablets comprising 1, 2, 2.5, 3, 4, 5, 6, 7.5, and 10 mg of warfarin. The INR may be adjusted to 2.0-4.5, or 2.0-3.0 or 2.5-3.5 depending on whether the warfarin is being administered to treat venous thromboembolism, non-valvular atrial fibrillation, post-myocardial infarction, heart valve prophylaxis, or recurrent systemic embolism.

In the PT test, a reagent which induces coagulation is added to a sample of the patient's plasma. The reagent typically primarily comprises thromboplastin and calcium chloride. Many commercially available PT reagents contain crude thromboplastin extracted from natural sources, e.g., rabbit brain, rabbit brain/lung mixtures, human placenta, or bovine brain, although recombinant thromboplastin may also be employed. Prothrombin time assays are performed by mixing the plasma sample and reagent at a constant temperature such as 37° C., and monitoring the progress of the reaction until a perceptible clot (or "gel clot") is detected. The development of a gel clot is the end point of the reaction. This end point may be detected in various ways such as by viscosity change, by electrode reaction, and, most commonly, by photometric means. The test result is generally compared to a result using a normal (control) plasma and converted to an INR.

The International Normalized Ratio, or INR, was developed to standardize PT values, so that test results from different thromboplastins and coagulation analyzers become equivalent. Under the INR system, a thromboplastin is assigned an International Sensitivity Index (ISI) value. The ISI indicates the relative sensitivity of the thromboplastin compared to an international reference thromboplastin. If a thromboplastin has the same sensitivity as the reference thromboplastin, then its ISI is 1.0. A higher ISI value indicates that a thromboplastin is less sensitive than the reference thromboplastin. The ISI is used in the following formula to calculate an INR value from a PT value: INR= (patient PT/mean normal PT)$^{ISI}$. The ISI is usually determined by the thromboplastin manufacturer. Different ISI values are assigned for different models or classes of coagulation analyzers.

In another embodiment, the active agent comprises phenytoin. Phenyloin, 5,5-diphenylhydantoin, is an antiepileptic active agent useful in the treatment of epilepsy which is eliminated by metabolism by cytochrome p450 isoforms including CYP1A2, CYP2C9, CYP2C19, and CYP3A4. Phenytoin has a narrow therapeutic index such that too little can lead to insufficient results and excessive phenytoin can lead to phenytoin toxicity. The typical clinically effective serum level is about 10 to about 20 μg/mL. The recommended initial dose is one 100 mg capsule 3 to 4 times per day, with 300 mg/day dose in three divided doses or one single dose per day. The dosing of phenytoin can be individualized according to the patient's sensitivity to the active agent by measuring plasma concentration of phenytoin.

Methods of treating a musculoskeletal condition or head pain with metaxalone are provided herein. Such methods include informing a user that metaxalone affects the activity of a cytochrome p450 isozyme. The method may further include informing the user that administration of metaxalone with a substance can affect the plasma concentration, bioavailability, safety, efficacy, or a combination comprising at least one of the foregoing of metaxalone or the substance. The method may also include informing the user of any information disclosed herein about the effect of metaxalone or the substance on the activity of a cytochrome p450 isozyme and any information disclosed herein about the effect of metaxalone or the substance on the plasma concentration, bioavailability, safety, efficacy, or a combination comprising at least one of the foregoing of metaxalone or the substance. Methods of treatment may also include providing a user with metaxalone or administering metaxalone to a patient.

Methods of treatment include methods in which the user is a patient and additionally comprising administering metaxalone and an active agent to the patient. The patient may be, for example, a human patient, a patient in need of treatment of a musculoskeletal condition or head pain, a patient receiving prophylactic metaxalone treatment, or a patient undergoing metaxalone therapy. The amount of metaxalone administered may be a therapeutically effective amount.

Methods of treatment may additionally include monitoring the patient's plasma concentration of the active agent as $AUC_{0-INF}$, $AUC_{0-t}$, $C_{MAX}$, or a combination of any of the foregoing pharmacokinetic parameters. When metaxalone is administered together with another active agent, methods of treatment can include determining the plasma concentration of the active agent and altering dosing of the active agent for the patient based on the determined active agent plasma concentration.

In another embodiment, a method of treatment comprises administering to a patient in need of both a skeletal muscle relaxant and an anticoagulant, for example, metaxalone and warfarin, and monitoring the Prothrombin Time/International Normalized Ratio. Monitoring the Prothrombin Time/International Normalized Ratio may be performed for example daily, every other day, weekly, every other week, monthly, or according to another schedule or time criteria. The method may further comprise providing to the patient or medical care worker instructions regarding measuring the Prothrombin Time/International Normalized Ratio.

When the substance administered with metaxalone is an NTI active agent, methods using a blood test to monitor plasma levels of the NTI active agent comprise administering to a patient metaxalone and the NTI active agent, and monitoring the blood levels of the NTI active agent as $AUC_{0-t}$, $AUC_{0-INF}$, $C_{MAX}$, or a combination comprising one or more of the foregoing pharmacokinetic parameters.

In one embodiment, a method of using a blood test to monitor warfarin levels comprises administering to a patient in need of both a skeletal muscle relaxant and an anticoagulant both metaxalone and warfarin, and monitoring the blood levels of warfarin as $AUC_{0-t}$, $AUC_{0-INF}$, $C_{MAX}$, or a combination comprising one or more of the foregoing pharmacokinetic parameters.

In another embodiment, the substance is phenytoin, and a method using a blood test to monitor plasma levels of phenytoin comprise administering to a patient metaxalone and phenytoin, and monitoring the blood levels of phenytoin as $AUC_{0-t}$, $AUC_{0-INF}$, $C_{MAX}$, or a combination comprising one or more of the foregoing pharmacokinetic parameters.

In all of the embodiments herein, a medical care worker can determine the plasma concentration of an active agent by performing or ordering the performance of any suitable method. For example, the medical care worker could order a test using blood drawn from the patient for determining the plasma concentration of the active agent.

The invention is further illustrated by the following examples.

EXAMPLE 1

Determination of Human Cytochrome p450 Isozymes Using Metaxalone as a Substrate

The study of this example was performed to determine the metabolism of metaxalone by human cytochrome p450 isoforms CYP1A2, CYP2A6, CYP2C9, CYP2C19, CYP2D6, CYP2E1, and CYP3A4. Microsomes containing singly-expressed human CYP isoforms were incubated in the presence of metaxalone. The metabolism of metaxalone was evaluated by measuring the disappearance of metaxalone by high-performance liquid chromatography (HPLC).

Commercially available microsomes from baculovirus-infected insect cells containing singly-expressed recombinant wild-type (*1 allele) human CYP enzymes and cDNA-expressed human cytochrome p450 oxidoreductase [BD SUPERSOMES Enzymes; BD Biosciences Discovery Labware (Woburn, Mass.)] were used. For CYP2A6, CYP2C9, CYP2C19, and CYP2E1, the SUPERSOMES also expressed human cytochrome b5 in addition to human cytochrome p450 oxidoreductase and the human CYP isozyme.

Metaxalone stock solutions were prepared in methanol at 100 times (100×) the final concentration. The stock solutions were added to incubation mixtures to obtain final concentrations of 0.5, 2.5, and 25 µM (corresponding to 111, 552, and 5530 ng metaxalone/mL, respectively), each containing 1% methanol. All incubations were conducted at 37±1° C. in a shaking water bath with a sample size of N=3 replicates for each experimental group. Incubation mixtures of microsomes (corresponding to 10 pmol p450) and metaxalone were prepared in 0.1 M Tris buffer. After a 5-minute pre-incubation, an NADPH regenerating system (NRS) was added to the incubation mixtures to initiate reactions, with a final incubation volume of 0.5 mL. Incubations were continued for 30 minutes, and then terminated, except for those for CYP2C19, which were incubated for 36 minutes prior to termination. Samples were then analyzed for metaxalone.

Positive controls with a suitable isoform-selective substrate were performed for each CYP isoform to verify metabolic activity. Concentration of metabolites formed from CYP isoform-selective substrates in the positive control samples was analyzed using liquid chromatography/mass spectrometry (LC/MS) or HPLC, as appropriate. A table of the substrate, substrate concentration, solvent, metabolite formed, and metabolite assay method for each CYP isozyme studied is below.

| CYP isoform | Isoform-selective substrate | Substrate concentration | Solvent | Metabolite formed | Metabolite Assay |
|---|---|---|---|---|---|
| CYP1A2 | Phenacetin | 50 µM | ACN | Acetaminophen | LC/MS |
| CYP2A6 | Coumarin | 8 µM | ACN | 7-hydroxy coumarin | HPLC-UV |
| CYP2C9 | Tolbutamide | 150 µM | ACN | 4'-methylhydroxytolbutamide | LC/MS |
| CYP2C19 | S-Mephenytoin | 50 µM | ACN | 4'-hydroxy mephenytoin | LC/MS |
| CYP2D6 | Dextromethorphan | 5 µM | Water | dextrorphan | LC/MS |
| CYP2E1 | Chlorzoxazone | 50 µM | ACN | 6-hydroxy chlorzoxazone | LC/MS |
| CYP3A4 | Testosterone | 100 µM | ACN | 6β-hydroxy testosterone | HPLC-UV |

Matrix controls were performed to determine the background signal from the matrix components (microsomes (10 pmol p450), 0.1N Tris buffer, NRS, and 1% methanol). Additionally metabolic negative controls were performed to distinguish potential nonenzymatic metabolism of metaxalone from p450-mediated metabolism. Incubation mixtures were prepared in 0.1 M Tris buffer with SUPERSOMES (10 pmol P450) and metaxalone (at each concentration). After a 5-minute pre-incubation, 2% sodium bicarbonate solution was added to the incubation mixtures. Incubation was for 30 minutes at a final volume of 0.5 mL. Matrix and metabolic negative controls were terminated by adding an equal volume of methanol. The matrix control and metabolic negative control samples were analyzed for metaxalone by HPLC. Analysis of samples was subsequent to storage at −70° C.

Results are presented for each studied human cytochrome p450 isozyme in Tables 2-8.

TABLE 2

Metabolism of Metaxalone by Expressed Recombinant Human CYP1A2

| Metaxalone Concentration (μM) | Metaxalone Present | | | Percent of Metabolic Negative Control | |
|---|---|---|---|---|---|
| | Raw (μM) | Adjusted (μM) | | | |
| | | Individual | Mean ± SD | Individual | Mean ± SD |
| MNC (0.5) | 0.20195 | 0.404 | 0.391 ± 0.0113 | 103 | 100 ± 2.88 |
| | 0.19430 | 0.389 | | 99.3 | |
| | 0.19097 | 0.382 | | 97.6 | |
| 0.5 | 0.15087 | 0.302 | 0.352 ± 0.0761 | 77.1 | 89.9 ± 19.4 |
| | 0.21975 | 0.440 | | 112 | |
| | 0.15734 | 0.315 | | 80.4 | |
| MNC (2.5) | 0.65183 | 1.30 | 1.33 ± 0.0221 | 98.3 | 100 ± 1.67 |
| | 0.66350 | 1.33 | | 100 | |
| | 0.67394 | 1.35 | | 102 | |
| 2.5 | 0.52700 | 1.05 | 1.07 ± 0.0167 | 79.5 | 80.4 ± 1.26 |
| | 0.52908 | 1.06 | | 79.8 | |
| | 0.54235 | 1.08 | | 81.8 | |
| MNC (25) | 10.11453 | 20.2 | 19.8 ± 0.360 | 102 | 100 ± 1.82 |
| | 9.76568 | 19.5 | | 98.5 | |
| | 9.86156 | 19.7 | | 99.5 | |
| 25 | 8.20521 | 16.4 | 16.6 ± 0.337 | 82.8 | 83.7 ± 1.70 |
| | 8.19232 | 16.4 | | 82.6 | |
| | 8.49030 | 17.0 | | 85.6 | |
| MXC (0) | 0.00000[a] | N/A | N/A ± N/A | N/A | N/A ± N/A |
| | 0.00000[a] | N/A | | N/A | |
| | 0.00000[a] | N/A | | N/A | |

Abbreviations:

SD, standard deviation;

MNC, metabolic negative control;

MXC, matrix control;

N/A, not applicable

[a]The Raw value (μM) was below the lowest concentration on the standard curve (0.05 μM).

Note:

For all calculations above, the resulting values are shown with at least three significant figures for display purposes only.

TABLE 3

Metabolism of Metaxalone by Expressed Recombinant Human CYP2A6

| Metaxalone Concentration (μM) | Metaxalone Present | | | Percent of Metabolic Negative Control | |
|---|---|---|---|---|---|
| | Raw (μM) | Adjusted (μM) | | | |
| | | Individual | Mean ± SD | Individual | Mean ± SD |
| MNC (0.5) | 0.15455 | 0.309 | 0.311 ± 0.00446 | 99.4 | 100 ± 1.43 |
| | 0.15795 | 0.316 | | 102 | |
| | 0.15375 | 0.308 | | 98.9 | |
| 0.5 | 0.15457 | 0.309 | 0.299 ± 0.0124 | 99.5 | 96.1 ± 3.99 |
| | 0.15112 | 0.302 | | 97.2 | |
| | 0.14253 | 0.285 | | 91.7 | |
| MNC (2.5) | 0.74261 | 1.49 | 1.52 ± 0.0353 | 97.9 | 100 ± 2.33 |
| | 0.75568 | 1.51 | | 99.6 | |
| | 0.77755 | 1.56 | | 102 | |
| 2.5 | 0.79130 | 1.58 | 1.61 ± 0.0373 | 104 | 106 ± 2.46 |
| | 0.79791 | 1.60 | | 105 | |
| | 0.82642 | 1.65 | | 109 | |
| MNC (25) | 7.74594 | 15.5 | 15.3 ± 0.147 | 101 | 100 ± 0.959 |
| | 7.64948 | 15.3 | | 99.8 | |
| | 7.60163 | 15.2 | | 99.2 | |
| 25 | 7.76399 | 15.5 | 15.6 ± 0.0975 | 101 | 102 ± 0.636 |
| | 7.85044 | 15.7 | | 102 | |
| | 7.84628 | 15.7 | | 102 | |

TABLE 3-continued

Metabolism of Metaxalone by Expressed Recombinant Human CYP2A6

| Metaxalone Concentration (µM) | Raw (µM) | Metaxalone Present Adjusted (µM) | | Percent of Metabolic Negative Control | |
|---|---|---|---|---|---|
| | | Individual | Mean ± SD | Individual | Mean ± SD |
| MXC (0) | 0.00000[a] | N/A | N/A ± N/A | N/A | N/A ± N/A |
| | 0.00000[a] | N/A | | N/A | |
| | 0.00000[a] | N/A | | N/A | |

Abbreviations:
SD, standard deviation;
MNC, metabolic negative control;
MXC, matrix control;
N/A, not applicable
[a]The Raw value (µM) was below the lowest concentration on the standard curve (0.05 µM)

Note:
For all calculations above, the resulting values are shown with at least three significant figures for display purposes only.

TABLE 4

Metabolism of Metaxalone by Expressed Recombinant Human CYP2C9

| Metaxalone Concentration (µM) | Raw (µM) | Metaxalone Present Adjusted (µM) | | Percent of Metabolic Negative Control | |
|---|---|---|---|---|---|
| | | Individual | Mean ± SD | Individual | Mean ± SD |
| MNC (0.5) | 0.17052 | 0.341 | 0.348 ± 0.00997 | 97.9 | 100 ± 2.86 |
| | 0.17229 | 0.345 | | 98.9 | |
| | 0.17990 | 0.360 | | 103 | |
| 0.5 | 0.18004 | 0.360 | 0.355 ± 0.00608 | 103 | 102 ± 1.75 |
| | 0.17784 | 0.356 | | 102 | |
| | 0.17403 | 0.348 | | 99.9 | |
| MNC (2.5) | 0.93197 | 1.86 | 1.93 ± 0.0605 | 96.8 | 100 ± 3.14 |
| | 0.96526 | 1.93 | | 100 | |
| | 0.99235 | 1.98 | | 103 | |
| 2.5 | 0.96842 | 1.94 | 1.92 ± 0.0246 | 101 | 99.7 ± 1.28 |
| | 0.96593 | 1.93 | | 100 | |
| | 0.94597 | 1.89 | | 98.2 | |
| MNC (25) | 10.31249 | 20.6 | 21.3 ± 0.620 | 97.1 | 100 ± 2.92 |
| | 10.63201 | 21.3 | | 100 | |
| | 10.93245 | 21.9 | | 103 | |
| 25 | 10.66111 | 21.3 | 21.5 ± 0.144 | 100 | 101 ± 0.675 |
| | 10.80454 | 21.6 | | 102 | |
| | 10.72836 | 21.5 | | 101 | |
| MXC (0) | 0.00000[a] | N/A | N/A ± N/A | N/A | N/A ± N/A |
| | 0.00000[a] | N/A | | N/A | |
| | 0.00000[a] | N/A | | N/A | |

Abbreviations:
SD, standard deviation;
MNC, metabolic negative control;
MXC, matrix control;
N/A, not applicable
[a]The Raw value (µM) was below the lowest concentration on the standard curve (0.05 µM)

Note:
For all calculations above, the resulting values are shown with at least three significant figures for display purposes only.

TABLE 5

Metabolism of Metaxalone by Expressed Recombinant Human CYP2C19

| Metaxalone Concentration (μM) | Metaxalone Present | | | Percent of Metabolic Negative Control | |
|---|---|---|---|---|---|
| | Raw (μM) | Adjusted (μM) Individual | Mean ± SD | Individual | Mean ± SD |
| MNC (0.5) | 0.18718 | 0.374 | 0.370 ± 0.00898 | 101 | 100 ± 2.43 |
| | 0.18763 | 0.375 | | 102 | |
| | 0.17964 | 0.359 | | 97.2 | |
| 0.5 | 0.16773 | 0.335 | 0.345 ± 0.0104 | 90.8 | 93.4 ± 2.82 |
| | 0.17180 | 0.344 | | 93.0 | |
| | 0.17808 | 0.356 | | 96.4 | |
| MNC (2.5) | 0.72720 | 1.45 | 1.39 ± 0.0560 | 105 | 100 ± 4.03 |
| | 0.67562 | 1.35 | | 97.2 | |
| | 0.68261 | 1.37 | | 98.2 | |
| 2.5 | 0.67218 | 1.34 | 1.34 ± 0.00561 | 96.7 | 96.5 ± 0.404 |
| | 0.67254 | 1.35 | | 96.7 | |
| | 0.66751 | 1.34 | | 96.0 | |
| MNC (25) | 9.84488 | 19.7 | 20.1 ± 1.03 | 97.8 | 100 ± 5.13 |
| | 9.69255 | 19.4 | | 96.3 | |
| | 10.65287 | 21.3 | | 106 | |
| 25 | 9.34508 | 18.7 | 18.6 ± 0.120 | 92.9 | 92.6 ± 0.597 |
| | 9.35948 | 18.7 | | 93.0 | |
| | 9.24903 | 18.5 | | 91.9 | |
| MXC (0) | 0.00000[a] | N/A | N/A ± N/A | N/A | N/A ± N/A |
| | 0.00000[a] | N/A | | N/A | |
| | 0.06454 | N/A | | N/A | |

Abbreviations:
SD, standard deviation;
MNC, metabolic negative control;
MXC, matrix control;
N/A, not applicable
[a] The Raw value (μM) was below the lowest concentration on the standard curve (0.05 μM)
Note:
For all calculations above, the resulting values are shown with at least three significant figures for display purposes only.

TABLE 6

Metabolism of Metaxalone by Expressed Recombinant Human CYP2D6

| Metaxalone Concentration (μM) | Metaxalone Present | | | Percent of Metabolic Negative Control | |
|---|---|---|---|---|---|
| | Raw (μM) | Adjusted (μM) Individual | Mean ± SD | Individual | Mean ± SD |
| MNC (0.5) | 0.14509 | 0.290 | 0.292 ± 0.00220 | 99.4 | 100 ± 0.755 |
| | 0.14716 | 0.294 | | 101 | |
| | 0.14547 | 0.291 | | 99.7 | |
| 0.5 | 0.18683 | 0.374 | 0.319 ± 0.0477 | 128 | 109 ± 16.3 |
| | 0.14857 | 0.297 | | 102 | |
| | 0.14305 | 0.286 | | 98.0 | |
| MNC (2.5) | 0.79025 | 1.58 | 1.56 ± 0.0184 | 101 | 100 ± 1.18 |
| | 0.78433 | 1.57 | | 100 | |
| | 0.77221 | 1.54 | | 98.7 | |
| 2.5 | 0.75826 | 1.52 | 1.53 ± 0.0111 | 96.9 | 97.7 ± 0.707 |
| | 0.76852 | 1.54 | | 98.2 | |
| | 0.76697 | 1.53 | | 98.0 | |
| MNC (25) | 9.63762 | 19.3 | 19.2 ± 0.0994 | 100 | 100 ± 0.517 |
| | 9.54788 | 19.1 | | 99.4 | |
| | 9.62976 | 19.3 | | 100 | |
| 25 | 9.52577 | 19.1 | 19.2 ± 0.436 | 99.2 | 99.9 ± 2.27 |
| | 9.84529 | 19.7 | | 103 | |
| | 9.42917 | 18.9 | | 98.2 | |

TABLE 6-continued

Metabolism of Metaxalone by Expressed Recombinant Human CYP2D6

| Metaxalone Concentration ($\mu$M) | Raw ($\mu$M) | Metaxalone Present | | Percent of Metabolic Negative Control | |
|---|---|---|---|---|---|
| | | Adjusted ($\mu$M) | | | |
| | | Individual | Mean ± SD | Individual | Mean ± SD |
| MXC (0) | 0.00000[a] | N/A | N/A ± N/A | N/A | N/A ± N/A |
| | 0.00000[a] | N/A | | N/A | |
| | 0.00000[a] | N/A | | N/A | |

Abbreviations:
SD, standard deviation;
MNC, metabolic negative control;
MXC, matrix control;
N/A, not applicable
[a]The Raw value ($\mu$M) was below the lowest concentration on the standard curve (0.05 $\mu$M)
Note:
For all calculations above, the resulting values are shown with at least three significant figures for display purposes only.

TABLE 7

Metabolism of Metaxalone by Expressed Recombinant Human CYP2E1

| Metaxalone Concentration ($\mu$M) | Raw ($\mu$M) | Metaxalone Present | | Percent of Metabolic Negative Control | |
|---|---|---|---|---|---|
| | | Adjusted ($\mu$M) | | | |
| | | Individual | Mean ± SD | Individual | Mean ± SD |
| MNC (0.5) | 0.18358 | 0.367 | 0.355 ± 0.0104 | 103 | 100 ± 2.92 |
| | 0.17510 | 0.350 | | 98.6 | |
| | 0.17416 | 0.348 | | 98.1 | |
| 0.5 | 0.17871 | 0.357 | 0.352 ± 0.00648 | 101 | 99.0 ± 1.83 |
| | 0.17235 | 0.345 | | 97.0 | |
| | 0.17662 | 0.353 | | 99.4 | |
| MNC (2.5) | 0.89075 | 1.78 | 1.69 ± 0.117 | 105 | 100 ± 6.89 |
| | 0.77998 | 1.56 | | 92.2 | |
| | 0.86695 | 1.73 | | 102 | |
| 2.5 | 0.88299 | 1.77 | 1.76 ± 0.00318 | 104 | 104 ± 0.188 |
| | 0.87990 | 1.76 | | 104 | |
| | 0.88209 | 1.76 | | 104 | |
| MNC (25) | 9.11125 | 18.2 | 17.8 ± 0.410 | 103 | 100 ± 2.30 |
| | 8.70811 | 17.4 | | 98.0 | |
| | 8.84728 | 17.7 | | 99.5 | |
| 25 | 8.73183 | 17.5 | 19.2 ± 2.71 | 98.2 | 108 ± 15.3 |
| | 11.15149 | 22.3 | | 125 | |
| | 8.87878 | 17.8 | | 99.9 | |
| MXC (0) | 0.00000[a] | N/A | N/A ± N/A | N/A | N/A ± N/A |
| | 0.00000[a] | N/A | | N/A | |
| | 0.00000[a] | N/A | | N/A | |

Abbreviations:
SD, standard deviation;
MNC, metabolic negative control;
MXC, matrix control;
N/A, not applicable
[a]The Raw value ($\mu$M) was below the lowest concentration on the standard curve (0.05 $\mu$M)
Note:
For all calculations above, the resulting values are shown with at least three significant figures for display purposes only.

TABLE 8

Metabolism of Metaxalone by Expressed Recombinant Human CYP3A4

| Metaxalone Concentration ($\mu$M) | Raw ($\mu$M) | Metaxalone Present Adjusted ($\mu$M) | | Percent of Metabolic Negative Control | |
|---|---|---|---|---|---|
| | | Individual | Mean ± SD | Individual | Mean ± SD |
| MNC (0.5) | 0.16014 | 0.320 | 0.318 ± 0.00502 | 101 | 100 ± 1.58 |
| | 0.15592 | 0.312 | | 98.2 | |
| | 0.16039 | 0.321 | | 101 | |
| 0.5 | 0.15978 | 0.320 | 0.320 ± 0.00333 | 101 | 101 ± 1.05 |
| | 0.16159 | 0.323 | | 102 | |
| | 0.15826 | 0.317 | | 99.6 | |
| MNC (2.5) | 0.85285 | 1.71 | 1.72 ± 0.0127 | 99.3 | 100 ± 0.741 |
| | 0.86553 | 1.73 | | 101 | |
| | 0.85828 | 1.72 | | 99.9 | |
| 2.5 | 0.85730 | 1.71 | 1.68 ± 0.0289 | 99.8 | 98.0 ± 1.68 |
| | 0.82923 | 1.66 | | 96.5 | |
| | 0.83738 | 1.67 | | 97.5 | |
| MNC (25) | 8.65154 | 17.3 | 17.4 ± 0.0906 | 99.4 | 100 ± 0.521 |
| | 8.71767 | 17.4 | | 100 | |
| | 8.73830 | 17.5 | | 100 | |
| 25 | 8.53809 | 17.1 | 17.1 ± 0.192 | 98.1 | 98.1 ± 1.10 |
| | 8.44686 | 16.9 | | 97.1 | |
| | 8.63905 | 17.3 | | 99.3 | |
| MXC (0) | 0.00000[a] | N/A | N/A ± N/A | N/A | N/A ± N/A |
| | 0.00000[a] | N/A | | N/A | |
| | 0.00000[a] | N/A | | N/A | |

Abbreviations:
SD, standard deviation;
MNC, metabolic negative control;
MXC, matrix control;
N/A, not applicable
[a]The Raw value ($\mu$M) was below the lowest concentration on the standard curve (0.05 $\mu$M)
Note:
For all calculations above, the resulting values are shown with at least three significant figures for display purposes only.

Tables 2 and 5 show the results for human CYP1A2 and CYP2C19, respectively. The results for these two cytochrome p450 isozymes show that metaxalone is a substrate for the enzymatic activity of both CYP1A2 and CYP2C19.

Disappearance of metaxalone was detected following incubation with CYP1A2 in the presence of the NADPH-regenerating system. Disappearance of metaxalone ranged from 10.1% to 19.6% (Table 2). The difference from the starting amount is statistically significant at 2.5 and 25 $\mu$M using an unpaired two-tailed t-test (p$\leq$0.05). These results indicate that CYP1A2 is involved in the metabolism of metaxalone.

In the experiments with CYP2C19, metaxalone disappearance was evident following incubation with metaxalone at all three concentrations (Table 5). The mean disappearance of metaxalone was 6.6% for the reaction using 0.5 $\mu$M metaxalone; the reduction in the mean amount of metaxalone from the value for the corresponding metabolic negative control was statistically significant (p$\leq$0.05) using an unpaired two-tailed t-test. The amount of the disappearance of metaxalone observed at 2.5 or 25 $\mu$M was not statistically significant (p>0.05) compared to the mean values for the corresponding metabolic negative controls using a two-tailed t-test. These results indicate that CYP2C19 is also involved in the metabolism of metaxalone, though to a lesser extent than CYP1A2.

Experiments with the other tested cytochrome p450 isozymes (Tables 3-4 and 6-8) failed to show any statistically significant disappearance of metaxalone following incubation at the standard conditions, indicating that, within the limits of detection for these experiments, metaxalone was not used as a substrate by the other tested cytochrome p450 isozymes: CYP2A6, CYP2C9, CYP2D6, CYP2E1, and CYP3A4.

EXAMPLE 2

Metaxalone Inhibition of Cytochrome p450 Isozymes in Human Microsomes

The study of this example was performed to determine the potential of metaxalone to inhibit the activities of cytochrome p450 (CYP) isoforms CYP1A2, CYP2A6, CYP2B6, CYP2C8, CYP2C9, CYP2C19, CYP2D6, CYP2E1, and CYP3A4 in human liver microsomes. Human liver microsomes were incubated in the presence of metaxalone and a substrate selective for each CYP isoform. A table of the substrate, substrate concentration, solvent, metabolite formed and metabolite assay method for each CYP isozyme studied is below.

| CYP isoform | Isoform-selective substrate | Substrate concentration | Solvent | Metabolite formed | Metabolite Assay |
|---|---|---|---|---|---|
| CYP1A2 | Phenacetin | 50 μM | ACN | acetaminophen | LC/MS |
| CYP2A6 | Coumarin | 8 μM | ACN | 7-hydroxy coumarin | HPLC-UV |
| CYP2B6 | S-Mephenytoin | 1 mM | ACN | nirvanol | LC/MS |
| CYP2C8 | Paclitaxel | 5 μM | ACN | 6-hydroxy paclitaxel | LC/MS |
| CYP2C9 | Tolbutamide | 150 μM | ACN | 4'-methylhydroxytolbutamide | LC/MS |
| CYP2C19 | S-Mephenytoin | 50 μM | ACN | 4'-hydroxy mephenytoin | LC/MS |
| CYP2D6 | Dextromethorphan | 5 μM | Water | dextrorphan | LC/MS |
| CYP2E1 | Chlorzoxazone | 50 μM | ACN | 6-hydroxy chlorzoxazone | LC/MS |
| CYP3A4 | Testosterone | 100 μM | ACN | 6β-hydroxy testosterone | HPLC-UV |

Metaxalone stock solutions were prepared in methanol at 100 times (100×) the final concentration and added to incubation mixtures to obtain final concentrations of 0.3, 1, 3, 30, and 100 μM (corresponding to 66.3, 221, 663, 6630 and 22,100 ng metaxalone/mL, respectively), each containing 1% methanol.

Microsomes were prepared by differential centrifugation of liver homogenates pooled from at least ten human donors.

All metaxalone incubations were conducted at 37±1° C. in a shaking water bath using a sample size of N=3 replicates for experimental groups. Incubation mixtures were prepared in 0.1 M Tris buffer and contained microsomes (0.25 mg protein/mL for CYP2C9, CYP2D6, CYP2E1, and CYP3A4; 0.5 mg protein/mL for CYP1A2, CYP2A6, CYP2B6, CYP2C8, and CYP2C19), metaxalone (at each concentration), and a CYP isoform-selective substrate. After a 5 minute preincubation, NADPH regenerating system (NRS) was added to initiate the reaction. CYP2A6 and CYP3A4 incubations were for 10 minutes. All other incubations were for 30 minutes.

Incubations for CYP2C8 were terminated by adding 1.0 mL of ACN, while all other incubations were terminated by adding 1.0 mL of methanol. Samples were transferred to cryovials and analyzed after storage at −70° C. Triplicate replicates were performed for each concentration of metaxalone for each cytochrome p450 isozyme.

To verify that the test system was responsive to inhibitors, a positive control using 1 μM ketoconazole, a selective inhibitor of CYP3A4, was added to CYP3A4 microsome incubations with 100 μM testosterone. Four replicates were performed. The test system was considered responsive to inhibitors since the mean specific activity of CYP3A4 in the positive control samples treated with ketoconazole was <14% of the mean specific activity in the corresponding vehicle control samples.

Vehicle control experiments were performed to establish a baseline value for enzyme activity. Incubation mixtures were prepared in 0.1 M Tris buffer with microsomes (0.25 mg protein/mL for CYP2C9, CYP2D6, CYP2E1, and CYP3A4; 0.5 mg protein/mL for CYP1A2, CYP2A6, CYP2B6, CYP2C8, and CYP2C19), 1% methanol, and a CYP isoform-selective substrate. Four replicates were performed.

Metaxalone interference control samples were also included to eliminate the possibility of interference by metaxalone or its metabolites in detection of the metabolite formed from an isoform-selective substrate. Two replicates were performed. Incubation mixtures containing microsomes (0.25 mg protein/mL for CYP2C9, CYP2D6, CYP2E1, and CYP3A4; 0.5 mg protein/mL for CYP1A2, CYP2A6, CYP2B6, CYP2C8, and CYP2C19), 100 μM metaxalone, and 1% substrate solvent were prepared in 0.1 M Tris buffer. No interference was detected in any of the metabolite assay methods used.

Results for each CYP isoform, in the presence and absence of metaxalone, are reported in Tables 9-17.

TABLE 9

CYP1A2 Activity in Pooled Human Microsomes

| Metaxalone (μM) | Acetaminophen formation | | | Specific Activity (pmol/min/mg protein) | | Percent of VC |
|---|---|---|---|---|---|---|
| | Raw (μM) | Adjusted (μM) | | | | |
| | | Individual | Mean ± SD | Individual | Mean ± SD | |
| 0 (VC) | 0.23653 | 0.237 | 0.216 ± 0.0138 | 31.5 | 28.8 ± 1.84 | 100 |
| | 0.21124 | 0.211 | | 28.2 | | |
| | 0.21156 | 0.212 | | 28.2 | | |
| | 0.20568 | 0.206 | | 27.4 | | |
| 0.3 | 0.21120 | 0.211 | 0.210 ± 0.00536 | 28.2 | 28.0 ± 0.715 | 97.2 |
| | 0.21487 | 0.215 | | 28.6 | | |
| | 0.20431 | 0.204 | | 27.2 | | |
| 1 | 0.19966 | 0.200 | 0.200 ± 0.00246 | 26.6 | 26.6 ± 0.327 | 92.3 |
| | 0.19709 | 0.197 | | 26.3 | | |
| | 0.20200 | 0.202 | | 26.9 | | |
| 3 | 0.19900 | 0.199 | 0.195 ± 0.00589 | 26.5 | 26.0 ± 0.785 | 90.3 |
| | 0.18839 | 0.188 | | 25.1 | | |
| | 0.19813 | 0.198 | | 26.4 | | |
| 30 | 0.18924 | 0.189 | 0.194 ± 0.00544 | 25.2 | 25.9 ± 0.725 | 89.8 |
| | 0.19323 | 0.193 | | 25.8 | | |
| | 0.20000 | 0.200 | | 26.7 | | |

TABLE 9-continued

CYP1A2 Activity in Pooled Human Microsomes

| Metaxalone (µM) | Raw (µM) | Acetaminophen formation Adjusted (µM) | | Specific Activity (pmol/min/mg protein) | | Percent of VC |
|---|---|---|---|---|---|---|
| | | Individual | Mean ± SD | Individual | Mean ± SD | |
| 100 | 0.17757 | 0.178 | 0.177 ± 0.000206 | 23.7 | 23.6 ± 0.0275 | 82.0 |
| | 0.17733 | 0.177 | | 23.6 | | |
| | 0.17716 | 0.177 | | 23.6 | | |

Abbreviations:
SD, standard deviation;
VC, vehicle control (1% Methanol).
Note:
For all calculations above, the resulting values are shown with at least three significant figures for display purposes only.

TABLE 10

CYP2A6 Activity in Pooled Human Microsomes

| Metaxalone (µM) | Raw (µM) | 7-Hydroxycoumarin formation Adjusted (µM) | | Specific Activity (pmol/min/mg protein) | | Percent of VC |
|---|---|---|---|---|---|---|
| | | Individual | Mean ± SD | Individual | Mean ± SD | |
| 0 (VC) | 1.03214 | 1.03 | 1.06 ± 0.0356 | 413 | 426 ± 14.2 | 100 |
| | 1.04464 | 1.04 | | 418 | | |
| | 1.06891 | 1.07 | | 428 | | |
| | 1.11282 | 1.11 | | 445 | | |
| 0.3 | 1.07439 | 1.07 | 1.03 ± 0.0399 | 430 | 413 ± 16.0 | 96.9 |
| | 0.99553 | 0.996 | | 398 | | |
| | 1.02457 | 1.02 | | 410 | | |
| 1 | 0.99854 | 0.999 | 1.02 ± 0.0184 | 399 | 407 ± 7.36 | 95.7 |
| | 1.02269 | 1.02 | | 409 | | |
| | 1.03468 | 1.03 | | 414 | | |
| 3 | 1.05100 | 1.05 | 1.09 ± 0.0402 | 420 | 436 ± 16.1 | 102 |
| | 1.13132 | 1.13 | | 453 | | |
| | 1.08822 | 1.09 | | 435 | | |
| 30 | 1.08205 | 1.08 | 1.14 ± 0.0493 | 433 | 455 ± 19.7 | 107 |
| | 1.15129 | 1.15 | | 461 | | |
| | 1.17736 | 1.18 | | 471 | | |
| 100 | 0.98864 | 0.989 | 1.01 ± 0.0416 | 395 | 404 ± 16.6 | 94.8 |
| | 0.98209 | 0.982 | | 393 | | |
| | 1.05713 | 1.06 | | 423 | | |

Abbreviations:
SD, standard deviation;
VC, vehicle control (1% Methanol)
Note:
For all calculations above, the resulting values are shown with at least three significant figures for display purposes only.

TABLE 11

CYP2B6 Activity in Pooled Human Microsomes

| Metaxalone (µM) | Raw (µM) | Nirvanol formation Adjusted (µM) | | Specific Activity (pmol/min/mg protein) | | Percent of VC |
|---|---|---|---|---|---|---|
| | | Individual | Mean ± SD | Individual | Mean ± SD | |
| 0 (VC) | 0.23500 | 0.235 | 0.225 ± 0.0120 | 31.3 | 29.9 ± 1.60 | 100 |
| | 0.23266 | 0.233 | | 31.0 | | |
| | 0.22199 | 0.222 | | 29.6 | | |
| | 0.20877 | 0.209 | | 27.8 | | |
| 0.3 | 0.20942 | 0.209 | 0.203 ± 0.00904 | 27.9 | 27.0 ± 1.21 | 90.2 |
| | 0.19234 | 0.192 | | 25.6 | | |
| | 0.20601 | 0.206 | | 27.5 | | |
| 1 | 0.20438 | 0.204 | 0.223 ± 0.0201 | 27.3 | 29.8 ± 2.68 | 99.5 |
| | 0.22144 | 0.221 | | 29.5 | | |
| | 0.24442 | 0.244 | | 32.6 | | |

TABLE 11-continued

CYP2B6 Activity in Pooled Human Microsomes

| Metaxalone (μM) | Raw (μM) | Adjusted (μM) Individual | Adjusted (μM) Mean ± SD | Specific Activity (pmol/min/mg protein) Individual | Specific Activity (pmol/min/mg protein) Mean ± SD | Percent of VC |
|---|---|---|---|---|---|---|
| 3 | 0.19695 | 0.197 | 0.203 ± 0.00751 | 26.3 | 27.1 ± 1.00 | 90.6 |
|  | 0.20166 | 0.202 |  | 26.9 |  |  |
|  | 0.21166 | 0.212 |  | 28.2 |  |  |
| 30 | 0.21681 | 0.217 | 0.217 ± 0.00162 | 28.9 | 28.9 ± 0.216 | 96.6 |
|  | 0.21548 | 0.215 |  | 28.7 |  |  |
|  | 0.21871 | 0.219 |  | 29.2 |  |  |
| 100 | 0.18648 | 0.186 | 0.188 ± 0.00436 | 24.9 | 25.1 ± 0.581 | 83.7 |
|  | 0.18463 | 0.185 |  | 24.6 |  |  |
|  | 0.19293 | 0.193 |  | 25.7 |  |  |

Abbreviations:
SD, standard deviation;
VC, vehicle control (1% Methanol)
Note:
For all calculations above, the resulting values are shown with at least three significant figures for display purposes only.

TABLE 12

CYP2C8 Activity in Pooled Human Microsomes

| Metaxalone (μM) | Raw (μM) | 6-Hydroxypaclitaxel formation Adjusted (μM) Individual | 6-Hydroxypaclitaxel formation Adjusted (μM) Mean ± SD | Specific Activity (pmol/min/mg protein) Individual | Specific Activity (pmol/min/mg protein) Mean ± SD | Percent of VC |
|---|---|---|---|---|---|---|
| 0 (VC) | 0.13462 | 0.135 | 0.136 ± 0.00522 | 17.9 | 18.2 ± 0.696 | 100 |
|  | 0.14017 | 0.140 |  | 18.7 |  |  |
|  | 0.14074 | 0.141 |  | 18.8 |  |  |
|  | 0.12965 | 0.130 |  | 17.3 |  |  |
| 0.3 | 0.14476 | 0.145 | 0.126 ± 0.0163 | 19.3 | 16.8 ± 2.18 | 92.7 |
|  | 0.11377 | 0.114 |  | 15.2 |  |  |
|  | 0.12042 | 0.120 |  | 16.1 |  |  |
| 1 | 0.13927 | 0.139 | 0.140 ± 0.00305 | 18.6 | 18.7 ± 0.406 | 103 |
|  | 0.13749 | 0.137 |  | 18.3 |  |  |
|  | 0.14343 | 0.143 |  | 19.1 |  |  |
| 3 | 0.15034 | 0.150 | 0.149 ± 0.00174 | 20.0 | 19.9 ± 0.232 | 109 |
|  | 0.14945 | 0.149 |  | 19.9 |  |  |
|  | 0.14698 | 0.147 |  | 19.6 |  |  |
| 30 | 0.14949 | 0.149 | 0.138 ± 0.0114 | 19.9 | 18.4 ± 1.52 | 101 |
|  | 0.13724 | 0.137 |  | 18.3 |  |  |
|  | 0.12667 | 0.127 |  | 16.9 |  |  |
| 100 | 0.13170 | 0.132 | 0.133 ± 0.0207 | 17.6 | 17.8 ± 2.76 | 97.8 |
|  | 0.15467 | 0.155 |  | 20.6 |  |  |
|  | 0.11340 | 0.113 |  | 15.1 |  |  |

Abbreviations:
SD, standard deviation;
VC, vehicle control (1% Methanol)
Note:
For all calculations above, the resulting values are shown with at least three significant figures for display purposes only.

TABLE 13

CYP2C9 Activity in Pooled Human Microsomes

| Metaxalone (μM) | Raw (μM) | 4'-Methylhydroxytolbutamide formation Adjusted (μM) Individual | 4'-Methylhydroxytolbutamide formation Adjusted (μM) Mean ± SD | Specific Activity (pmol/min/mg protein) Individual | Specific Activity (pmol/min/mg protein) Mean ± SD | Percent of VC |
|---|---|---|---|---|---|---|
| 0 (VC) | 0.17476 | 0.175 | 0.166 ± 0.0208 | 46.6 | 44.3 ± 5.54 | 100 |
|  | 0.14904 | 0.149 |  | 39.7 |  |  |

TABLE 13-continued

CYP2C9 Activity in Pooled Human Microsomes

| Metaxalone (μM) | 4'-Methylhydroxytolbutamide formation | | | Specific Activity | | Percent of VC |
|---|---|---|---|---|---|---|
| | Raw (μM) | Adjusted (μM) | | (pmol/min/mg protein) | | |
| | | Individual | Mean ± SD | Individual | Mean ± SD | |
| | 0.14954 | 0.150 | | 39.9 | | |
| | 0.19164 | 0.192 | | 51.1 | | |
| 0.3 | 0.13620 | 0.136 | 0.135 ± 0.00106 | 36.3 | 36.1 ± 0.283 | 81.4 |
| | 0.13415 | 0.134 | | 35.8 | | |
| | 0.13565 | 0.136 | | 36.2 | | |
| 1 | 0.15107 | 0.151 | 0.136 ± 0.0187 | 40.3 | 36.2 ± 4.98 | 81.6 |
| | 0.14080 | 0.141 | | 37.5 | | |
| | 0.11485 | 0.115 | | 30.6 | | |
| 3 | 0.13051 | 0.131 | 0.135 ± 0.0103 | 34.8 | 36.0 ± 2.75 | 81.2 |
| | 0.12759 | 0.128 | | 34.0 | | |
| | 0.14670 | 0.147 | | 39.1 | | |
| 30 | 0.14975 | 0.150 | 0.151 ± 0.00841 | 39.9 | 40.3 ± 2.24 | 91.0 |
| | 0.14376 | 0.144 | | 38.3 | | |
| | 0.16037 | 0.160 | | 42.8 | | |
| 100 | 0.16269 | 0.163 | 0.145 ± 0.0150 | 43.4 | 38.8 ± 4.00 | 87.4 |
| | 0.13711 | 0.137 | | 36.6 | | |
| | 0.13627 | 0.136 | | 36.3 | | |

Abbreviations:
SD, standard deviation;
VC, vehicle control (1% Methanol)
Note:
For all calculations above, the resulting values are shown with at least three significant figures for display purposes only.

TABLE 14

CYP2C19 Activity in Pooled Human Microsomes

| Metaxalone (μM) | 4'-Hydroxymephenytoin formation | | | Specific Activity | | Percent of VC |
|---|---|---|---|---|---|---|
| | Raw (μM) | Adjusted (μM) | | (pmol/min/mg protein) | | |
| | | Individual | Mean ± SD | Individual | Mean ± SD | |
| 0 | 0.16904 | 0.169 | 0.168 ± 0.00550 | 22.5 | 22.4 ± 0.733 | 100 |
| (VC) | 0.17373 | 0.174 | | 23.2 | | |
| | 0.16915 | 0.169 | | 22.6 | | |
| | 0.16055 | 0.161 | | 21.4 | | |
| 0.3 | 0.13971 | 0.140 | 0.142 ± 0.00299 | 18.6 | 19.0 ± 0.399 | 84.6 |
| | 0.14558 | 0.146 | | 19.4 | | |
| | 0.14164 | 0.142 | | 18.9 | | |
| 1 | 0.11367 | 0.114 | 0.113 ± 0.00140 | 15.2 | 15.0 ± 0.186 | 67.0 |
| | 0.11336 | 0.113 | | 15.1 | | |
| | 0.11111 | 0.111 | | 14.8 | | |
| 3 | 0.11597 | 0.116 | 0.114 ± 0.00238 | 15.5 | 15.2 ± 0.317 | 67.7 |
| | 0.11127 | 0.111 | | 14.8 | | |
| | 0.11423 | 0.114 | | 15.2 | | |
| 30 | 0.08336 | 0.0834 | 0.107 ± 0.0211 | 11.1 | 14.3 ± 2.82 | 63.8 |
| | 0.12339 | 0.123 | | 16.5 | | |
| | 0.11502 | 0.115 | | 15.3 | | |
| 100 | 0.10857 | 0.109 | 0.109 ± 0.00205 | 14.5 | 14.5 ± 0.274 | 64.9 |
| | 0.11132 | 0.111 | | 14.8 | | |
| | 0.10730 | 0.107 | | 14.3 | | |

Abbreviations:
SD, standard deviation;
VC, vehicle control (1% Methanol)
Note:
For all calculations above, the resulting values are shown with at least three significant figures for display purposes only.

TABLE 15

CYP2D6 Activity in Pooled Human Microsomes

| Metaxalone (µM) | Dextrorphan formation | | | Specific Activity | | Percent of VC |
|---|---|---|---|---|---|---|
| | Raw (µM) | Adjusted (µM) | | (pmol/min/mg protein) | | |
| | | Individual | Mean ± SD | Individual | Mean ± SD | |
| 0 (VC) | 0.18550 | 0.186 | 0.183 ± 0.00342 | 49.5 | 48.9 ± 0.911 | 100 |
| | 0.18569 | 0.186 | | 49.5 | | |
| | 0.18424 | 0.184 | | 49.1 | | |
| | 0.17843 | 0.178 | | 47.6 | | |
| 0.3 | 0.14820 | 0.148 | 0.149 ± 0.00258 | 39.5 | 39.8 ± 0.688 | 81.3 |
| | 0.14716 | 0.147 | | 39.2 | | |
| | 0.15206 | 0.152 | | 40.5 | | |
| 1 | 0.15910 | 0.159 | 0.154 ± 0.00482 | 42.4 | 41.2 ± 1.28 | 84.2 |
| | 0.14949 | 0.149 | | 39.9 | | |
| | 0.15485 | 0.155 | | 41.3 | | |
| 3 | 0.16116 | 0.161 | 0.164 ± 0.00353 | 43.0 | 43.7 ± 0.940 | 89.3 |
| | 0.16267 | 0.163 | | 43.4 | | |
| | 0.16788 | 0.168 | | 44.8 | | |
| 30 | 0.15533 | 0.155 | 0.156 ± 0.00335 | 41.4 | 41.6 ± 0.893 | 85.1 |
| | 0.15983 | 0.160 | | 42.6 | | |
| | 0.15328 | 0.153 | | 40.9 | | |
| 100 | 0.15992 | 0.160 | 0.158 ± 0.00255 | 42.6 | 42.0 ± 0.680 | 85.9 |
| | 0.15489 | 0.155 | | 41.3 | | |
| | 0.15813 | 0.158 | | 42.2 | | |

Abbreviations:
SD, standard deviation;
VC, vehicle control (1% Methanol)
Note:
For all calculations above, the resulting values are shown with at least three significant figures for display purposes only.

TABLE 16

CYP2E1 Activity in Pooled Human Microsomes

| Metaxalone (µM) | 6-Hydroxychlorzoxazone formation | | | Specific Activity | | Percent of VC |
|---|---|---|---|---|---|---|
| | Raw (µM) | Adjusted (µM) | | (pmol/min/mg protein) | | |
| | | Individual | Mean ± SD | Individual | Mean ± SD | |
| 0 (VC) | 0.85346 | 0.853 | 0.852 ± 0.0127 | 228 | 227 ± 3.39 | 100 |
| | 0.86925 | 0.869 | | 232 | | |
| | 0.84615 | 0.846 | | 226 | | |
| | 0.83969 | 0.840 | | 224 | | |
| 0.3 | 0.73634 | 0.736 | 0.710 ± 0.0228 | 196 | 189 ± 6.08 | 83.3 |
| | 0.69947 | 0.699 | | 187 | | |
| | 0.69469 | 0.695 | | 185 | | |
| 1 | 0.72701 | 0.727 | 0.716 ± 0.0194 | 194 | 191 ± 5.18 | 84.0 |
| | 0.72685 | 0.727 | | 194 | | |
| | 0.69326 | 0.693 | | 185 | | |
| 3 | 0.76089 | 0.761 | 0.755 ± 0.0110 | 203 | 201 ± 2.94 | 88.6 |
| | 0.74221 | 0.742 | | 198 | | |
| | 0.76169 | 0.762 | | 203 | | |
| 30 | 0.71716 | 0.717 | 0.733 ± 0.0145 | 191 | 196 ± 3.88 | 86.1 |
| | 0.74538 | 0.745 | | 199 | | |
| | 0.73733 | 0.737 | | 197 | | |
| 100 | 0.74969 | 0.750 | 0.743 ± 0.0175 | 200 | 198 ± 4.66 | 87.2 |
| | 0.75620 | 0.756 | | 202 | | |
| | 0.72321 | 0.723 | | 193 | | |

Abbreviations:
SD, standard deviation;
VC, vehicle control (1% Methanol)
Note:
For all calculations above, the resulting values are shown with at least three significant figures for display purposes only.

TABLE 17

CYP3A4 Activity in Pooled Human Microsomes

| Metaxalone (μM) | 6β-Hydroxytestosterone formation | | | Specific Activity | | Percent of VC |
|---|---|---|---|---|---|---|
| | Raw (μM) | Adjusted (μM) | | (pmol/min/mg protein) | | |
| | | Individual | Mean ± SD | Individual | Mean ± SD | |
| 0 (VC) | 0.12662* | N/A | 0.742 ± 0.00679 | N/A | 594 ± 5.43 | 100 |
| | 0.74589 | 0.746 | | 597 | | |
| | 0.74640 | 0.746 | | 597 | | |
| | 0.73440 | 0.734 | | 588 | | |
| 0.3 | 0.64318 | 0.643 | 0.647 ± 0.0130 | 515 | 517 ± 10.4 | 87.1 |
| | 0.66083 | 0.661 | | 529 | | |
| | 0.63550 | 0.636 | | 508 | | |
| 1 | 0.65762 | 0.658 | 0.654 ± 0.00353 | 526 | 523 ± 2.83 | 88.1 |
| | 0.65446 | 0.654 | | 524 | | |
| | 0.65057 | 0.651 | | 520 | | |
| 3 | 0.67154 | 0.672 | 0.668 ± 0.00420 | 537 | 534 ± 3.36 | 90.0 |
| | 0.66336 | 0.663 | | 531 | | |
| | 0.66907 | 0.669 | | 535 | | |
| 30 | 0.62513 | 0.625 | 0.633 ± 0.0370 | 500 | 506 ± 29.6 | 85.2 |
| | 0.67282 | 0.673 | | 538 | | |
| | 0.59996 | 0.600 | | 480 | | |
| 100 | 0.63960 | 0.640 | 0.596 ± 0.0454 | 512 | 477 ± 36.3 | 80.3 |
| | 0.59940 | 0.599 | | 480 | | |
| | 0.54904 | 0.549 | | 439 | | |

Abbreviations:
SD, standard deviation;
VC, vehicle control (1% Methanol)
*Sample has been removed from all calculations due to the incorrect volume being added to the sample to stop the reaction.
Note:
For all calculations above, the resulting values are shown with at least three significant figures for display purposes only.

Under these experimental conditions, metaxalone inhibited activities of CYP1A2, CYP2B6, CYP2C19, CYP2D6, CYP2E1, and CYP3A4 in human liver microsomes at one or more of the tested metaxalone concentrations at a statistically significant level ($p \leq 0.05$ using an unpaired two-tailed t-test). The inhibition ranged from 12.8% (CYP2E1) to 35.1% (CYP2C19) at a metaxalone concentration of 100 μM.

Under these experimental conditions, no tested concentration of metaxalone inhibited activity of CYP2A6, CYP2C8, or CYP2C9 in human liver microsomes at a statistically significant level ($p > 0.05$ using an unpaired two-tailed t-test).

EXAMPLE 3

Metaxalone Induction/Inhibition of Cytochrome p450 Isozymes

The study of this example was performed to determine if there is induction or inhibition by metaxalone of cytochrome p450 isozymes CYP1A2, CYP2A6, CYP2B6, CYP2C9, CYP2C19, CYP2D6, CYP2E1, and CYP3A4. These induction/inhibition studies used cryopreserved human hepatocytes and compared enzymatic activity levels for each of these cytochrome p450 isozymes, using an appropriate enzyme substrate, in the human hepatocytes following in vitro exposure for 48±3 hrs in the presence or absence of metaxalone.

Hepatocytes from three human donors were obtained from a cryopreserved hepatocyte bank (In Vitro Technologies, Inc., USA). After thawing, viable hepatocytes were transferred to collagen-coated 48-well plates for attachment in plating medium (DMEM stock (Dulbecco's modified Eagle's medium, supplemented with bovine serum albumin, fructose, N-(2-hydroxyethyl)piperazine-N'-(2-ethanesulfonate) (HEPES), and sodium bicarbonate), supplemented with antibiotics, bovine serum, hydrocortisone, insulin and minimum essential medium (MEM) nonessential amino acids). After attachment to the collagen matrix, plating medium was replaced with sandwich medium (plating medium supplemented with VITROGEN) and incubated until use. All incubations were conducted at 37±1° C., 95% air/5% $CO_2$ and saturating humidity.

After establishment of the hepatocyte culture, sandwich medium was removed and the hepatocytes were incubated with incubation solution (DMEM stock supplemented with antibiotics, hydrocortisone, insulin, and MEM non-essential amino acids) containing 0.4, 4.0, or 40 μM metaxalone for 24±1.5 hrs. Incubation solution was aspirated and replaced with incubation solution containing the same concentration of metaxalone and incubated for an additional 24±1.5 hrs. After the metaxalone treatment period, the incubation solution was replaced with 150 μL Krebs-Henseleit (KHB) buffer supplemented with antibiotics, calcium chloride, heptanoic acid, HEPES, and sodium bicarbonate (supplemented KHB) and incubated for 10 minutes. The supplemented KHB was replaced with 150 μL supplemented KHB containing the appropriate isoform-selective substrate and incubated for 4 hrs prior to termination by adding 150 μL ice-cold methanol, except for the CYP2C8 incubations which were terminated by adding 150 μL acetonitrile. Samples were transferred to cryovials and analyzed after storage at −70° C. Three induction replicates were performed at each metaxalone concentration for each cytochrome p450 isozyme.

A table of the substrate, substrate concentration, metabolite formed, and metabolite assay method for each CYP isozyme studied is provided below. All substrates were dissolved in acetonitrile.

| CYP isoform | Isoform-selective substrate | Substrate concentration | Metabolite formed | Metabolite Assay |
|---|---|---|---|---|
| CYP1A2 | Phenacetin | 100 μM | acetaminophen | LC/MS |
| CYP2A6 | Coumarin | 100 μM | 7-hydroxycoumarin, 7-hydroxycoumaringlucuronide, 7-hydroxycoumarin sulfate | HPLC-UV |
| CYP2B6 | S-Mephenytoin | 1 mM | nirvanol | LC/MS |
| CYP2C9 | Tolbutamide | 50 μM | 4'-methylhydroxytolbutamide | LC/MS |
| CYP2C19 | S-Mephenytoin | 100 μM | 4'-hydroxy mephenytoin | LC/MS |
| CYP2D6 | Dextromethorphan | 16 μM | dextrorphan | LC/MS |
| CYP2E1 | Chlorzoxazone | 300 μM | 6-hydroxychlorzoxazone | LC/MS |
| CYP3A4 | Testosterone | 125 μM | 6β-hydroxy testosterone | HPLC-UV |

Metaxalone 100× stock solutions were prepared in methanol as described above and diluted with incubation medium to produce incubation solutions with 0.4, 4.0, and 40 μM metaxalone.

Replicate trials and controls were performed. Positive controls (n=4) were performed to verify that the test system was sensitive to known inducers by testing induction of CYP1A2 and CYP3A4 using 50 μM omeprazole and 25 μM rifampicin, respectively, as inducers with the appropriate isoform-selective substrate. Both positive control test systems showed ≧200% induction. Additionally, reference control samples were included to evaluate inducibility of CYP2B6, CYP2C9, and CYP2C19 in the test system. The reference controls included 1 mM Phenobarbital (CYP2B6) or 25 μM rifampicin as the reference inducer. The reference controls showed a statistically significant amount of induction for each hepatocyte donor for CYP2B6 and CYP2C9, although the amount of induction varied between the three hepatocyte donors for each isozyme. For CYP2C19, rifampin induced CYP2C19 activity in donor 1 and donor 3, but did not induce CYP2C19 activity in donor 2 at a statistically significant level (p<0.05 using an unpaired two-tailed t-test).

Results for each cytochrome p450 isozyme are shown in Tables 18-25. Significant induction was observed at these experimental conditions in all three donors for CYP1A2 and in one donor for CYP3A4 at the highest tested concentration. Additionally, significant inhibition in enzyme activity was observed in all three donors for CYP2C9 and in two donors for CYP2D6. Under these experimental conditions, no significant effects on activity of CYP2A6, CYP2B6, CYP2C19, or CYP2E1 were observed after exposure to any of the tested concentrations of metaxalone. Significance of a change in specific activity from that measured for the vehicle control (0 μM metaxalone) was determined using a two-tailed t-test. Mean specific activity values with associated p-values ≦0.05 were deemed to be statistically significant.

TABLE 18

CYP1A2 Activity in Cryopreserved Human Hepatocytes

| Metaxalone (μM) | Acetaminophen formation | | | Specific Activity (pmol/min/million cells) | | Percent of VC |
|---|---|---|---|---|---|---|
| | Raw (μM) | Adjusted (μM) | | | | |
| | | Individual | Mean ± SD | Individual | Mean ± SD | |
| Donor 1 | | | | | | |
| 0 (VC) | 0.05388 | 0.0539 | 0.0487 ± 0.00543 | 0.481 | 0.435 ± 0.0485 | 100 |
| | 0.05227 | 0.0523 | | 0.467 | | |
| | 0.04658 | 0.0466 | | 0.416 | | |
| | 0.04203 | 0.0420 | | 0.375 | | |
| 0.4 | 0.05121 | 0.0512 | 0.0537 ± 0.00309 | 0.457 | 0.479 ± 0.0276 | 110 |
| | 0.05264 | 0.0526 | | 0.470 | | |
| | 0.05714 | 0.0571 | | 0.510 | | |
| 4 | 0.07410 | 0.0741 | 0.0638 ± 0.0193 | 0.662 | 0.570 ± 0.172 | 131 |
| | 0.07581 | 0.0758 | | 0.677 | | |
| | 0.04160 | 0.0416 | | 0.371 | | |
| 40 | 0.15156 | 0.152 | 0.161 ± 0.0133 | 1.35 | 1.44 ± 0.119 | 332 |
| | 0.15617 | 0.156 | | 1.39 | | |
| | 0.17659 | 0.177 | | 1.58 | | |
| Donor 2 | | | | | | |
| 0 (VC) | 0.03023 | 0.0302 | 0.0300 ± 0.00305 | 0.270 | 0.267 ± 0.0272 | 100 |
| | 0.03210 | 0.0321 | | 0.287 | | |
| | 0.03193 | 0.0319 | | 0.285 | | |
| | 0.02556 | 0.0256 | | 0.228 | | |
| 0.4 | 0.03165 | 0.0317 | 0.0323 ± 0.000850 | 0.283 | 0.289 ± 0.00759 | 108 |
| | 0.03208 | 0.0321 | | 0.286 | | |
| | 0.03329 | 0.0333 | | 0.297 | | |
| 4 | 0.03346 | 0.0335 | 0.0340 ± 0.00198 | 0.299 | 0.304 ± 0.0177 | 113 |
| | 0.03619 | 0.0362 | | 0.323 | | |
| | 0.03234 | 0.0323 | | 0.289 | | |
| 40 | 0.06015 | 0.0602 | 0.0589 ± 0.00795 | 0.537 | 0.526 ± 0.0710 | 197 |

TABLE 18-continued

CYP1A2 Activity in Cryopreserved Human Hepatocytes

| Metaxalone (μM) | Acetaminophen formation | | | Specific Activity | | Percent of VC |
|---|---|---|---|---|---|---|
| | Raw (μM) | Adjusted (μM) | | (pmol/min/million cells) | | |
| | | Individual | Mean ± SD | Individual | Mean ± SD | |
| | 0.06616 | 0.0662 | | 0.591 | | |
| | 0.05040 | 0.0504 | | 0.450 | | |
| Donor 3 | | | | | | |
| 0 (VC) | 0.04357 | 0.0436 | 0.0410 ± 0.00447 | 0.389 | 0.366 ± 0.0399 | 100 |
| | 0.04576 | 0.0458 | | 0.409 | | |
| | 0.03607 | 0.0361 | | 0.322 | | |
| | 0.03849 | 0.0385 | | 0.344 | | |
| 0.4 | 0.04030 | 0.0403 | 0.0438 ± 0.00361 | 0.360 | 0.391 ± 0.0322 | 107 |
| | 0.04347 | 0.0435 | | 0.388 | | |
| | 0.04750 | 0.0475 | | 0.424 | | |
| 4 | 0.04411 | 0.0441 | 0.0443 ± 0.000214 | 0.394 | 0.396 ± 0.00191 | 108 |
| | 0.04453 | 0.0445 | | 0.398 | | |
| | 0.04425 | 0.0443 | | 0.395 | | |
| 40 | 0.12276 | 0.123 | 0.122 ± 0.00365 | 1.10 | 1.09 ± 0.0326 | 297 |
| | 0.11776 | 0.118 | | 1.05 | | |
| | 0.12487 | 0.125 | | 1.11 | | |

Abbreviations:
SD, standard deviation;
VC, vehicle control (1% Methanol)
Note:
For all calculations above, the resulting values are shown with at least three significant figures for display purposes only.

TABLE 19

CYP2A6 Activity in Cryopreserved Human Hepatocytes

| Metaxalone (μM) | Total Metabolite formation | | | Specific Activity | | Percent of VC |
|---|---|---|---|---|---|---|
| | Raw (μM) | Adjusted (μM) | | (pmol/min/million cells) | | |
| | | Individual | Mean ± SD | Individual | Mean ± SD | |
| Total Metabolite Formation: Donor 1 | | | | | | |
| 0 (VC) | 0.0171[d] | <0.300 | <0.300 ± 0.000 | <2.68 | <2.68 ± 0.000 | 100 |
| | 0.000[d] | <0.300 | | <2.68 | | |
| | 0.000[d] | <0.300 | | <2.68 | | |
| | 0.000[d] | <0.300 | | <2.68 | | |
| 0.4 | 0.000[d] | <0.300 | <0.300 ± 0.000 | <2.68 | <2.68 ± 0.000 | 100 |
| | 0.000[d] | <0.300 | | <2.68 | | |
| | 0.000[d] | <0.300 | | <2.68 | | |
| 4 | 0.000[d] | <0.300 | <0.300 ± 0.000 | <2.68 | <2.68 ± 0.000 | 100 |
| | 0.000[d] | <0.300 | | <2.68 | | |
| | 0.000[d] | <0.300 | | <2.68 | | |
| 40 | 0.000[d] | <0.300 | <0.300 ± 0.000 | <2.68 | <2.68 ± 0.000 | 100 |
| | 0.000[d] | <0.300 | | <2.68 | | |
| | 0.000[d] | <0.300 | | <2.68 | | |
| Total Metabolite Formation: Donor 2 | | | | | | |
| 0 (VC) | 0.0381[d] | <0.300 | <0.300 ± 0.000 | <2.68 | <2.68 ± 0.000 | 100 |
| | 0.0413[d] | <0.300 | | <2.68 | | |
| | 0.0365[d] | <0.300 | | <2.68 | | |
| | 0.0320[d] | <0.300 | | <2.68 | | |
| 0.4 | 0.0225[d] | <0.300 | <0.300 ± 0.000 | <2.68 | <2.68 ± 0.000 | 100 |
| | 0.0381[d] | <0.300 | | <2.68 | | |
| | 0.0381[d] | <0.300 | | <2.68 | | |
| 4 | 0.0344[d] | <0.300 | <0.300 ± 0.000 | <2.68 | <2.68 ± 0.000 | 100 |
| | 0.0353[d] | <0.300 | | <2.68 | | |
| | 0.0297[d] | <0.300 | | <2.68 | | |
| 40 | 0.0293[d] | <0.300 | <0.300 ± 0.000 | <2.68 | <2.68 ± 0.000 | 100 |
| | 0.0266[d] | <0.300 | | <2.68 | | |
| | 0.0333[d] | <0.300 | | <2.68 | | |
| Total Metabolite Formation: Donor 3 | | | | | | |
| 0 (VC) | 0.000[d] | <0.300 | <0.300 ± 0.000 | <2.68 | <2.68 ± 0.000 | 100 |
| | 0.0196[d] | <0.300 | | <2.68 | | |

TABLE 19-continued

CYP2A6 Activity in Cryopreserved Human Hepatocytes

| Metaxalone (μM) | Total Metabolite formation | | | Specific Activity | | Percent of VC |
|---|---|---|---|---|---|---|
| | Raw (μM) | Adjusted (μM) | | (pmol/min/million cells) | | |
| | | Individual | Mean ± SD | Individual | Mean ± SD | |
| | 0.0237[d] | <0.300 | | <2.68 | | |
| | 0.000[d] | <0.300 | | <2.68 | | |
| 0.4 | 0.0216[d] | <0.300 | <0.300 ± 0.000 | <2.68 | <2.68 ± 0.000 | 100 |
| | 0.0182[d] | <0.300 | | <2.68 | | |
| | 0.0182[d] | <0.300 | | <2.68 | | |
| 4 | 0.000[d] | <0.300 | <0.300 ± 0.000 | <2.68 | <2.68 ± 0.000 | 100 |
| | 0.0197[d] | <0.300 | | <2.68 | | |
| | 0.0162[d] | <0.300 | | <2.68 | | |
| 40 | 0.000[d] | <0.300 | <0.300 ± 0.000 | <2.68 | <2.68 ± 0.000 | 100 |
| | 0.0188[d] | <0.300 | | <2.68 | | |
| | 0.000[d] | <0.300 | | <2.68 | | |

Abbreviations:
SD, standard deviation;
VC, vehicle control (1% Methanol)
[d]The observed analyzed value (μM) for all metabolites were below the lowest concentration on the corresponding standard curve.
Note:
For all calculations above, the resulting values are shown with at least three significant figures for display purposes only.

TABLE 20

CYP2B6 Activity in Cryopreserved Human Hepatocytes

| Metaxalone (μM) | Nirvanol formation | | | Specific Activity | | Percent of VC |
|---|---|---|---|---|---|---|
| | Raw (μM) | Adjusted (μM) | | (pmol/min/million cells) | | |
| | | Individual | Mean ± SD | Individual | Mean ± SD | |
| *Donor 1* | | | | | | |
| 0 (VC) | 0.03230 | 0.0323 | 0.0319 ± 0.00156 | 0.288 | 0.285 ± 0.0139 | 100 |
| | 0.03384 | 0.0338 | | 0.302 | | |
| | 0.03014 | 0.0301 | | 0.269 | | |
| | 0.03141 | 0.0314 | | 0.280 | | |
| 0.4 | 0.03380 | 0.0338 | 0.0340 ± 0.000883 | 0.302 | 0.304 ± 0.00789 | 107 |
| | 0.03329 | 0.0333 | | 0.297 | | |
| | 0.03501 | 0.0350 | | 0.313 | | |
| 4 | 0.02742 | 0.0274 | 0.0305 ± 0.00272 | 0.245 | 0.273 ± 0.0243 | 95.7 |
| | 0.03241 | 0.0324 | | 0.289 | | |
| | 0.03178 | 0.0318 | | 0.284 | | |
| 40 | 0.03233 | 0.0323 | 0.0310 ± 0.00204 | 0.289 | 0.277 ± 0.0182 | 97.1 |
| | 0.03203 | 0.0320 | | 0.286 | | |
| | 0.02866 | 0.0287 | | 0.256 | | |
| *Donor 2* | | | | | | |
| 0 (VC) | 0.02927 | 0.0293 | 0.0289 ± 0.00230 | 0.261 | 0.258 ± 0.0205 | 100 |
| | 0.02920 | 0.0292 | | 0.261 | | |
| | 0.03137 | 0.0314 | | 0.280 | | |
| | 0.02582 | 0.0258 | | 0.231 | | |
| 0.4 | 0.02544 | 0.0254 | 0.0306 ± 0.00559 | 0.227 | 0.273 ± 0.0499 | 106 |
| | 0.02986 | 0.0299 | | 0.267 | | |
| | 0.03654 | 0.0365 | | 0.326 | | |
| 4 | 0.02852 | 0.0285 | 0.0281 ± 0.000884 | 0.255 | 0.250 ± 0.00790 | 97.0 |
| | 0.02703 | 0.0270 | | 0.241 | | |
| | 0.02860 | 0.0286 | | 0.255 | | |
| 40 | 0.00341[a] | <0.0250 | <0.0250 ± 0.000 | <0.223 | <0.223 ± 0.000 | <86.5 |
| | 0.00320[a] | <0.0250 | | <0.223 | | |
| | 0.00330[a] | <0.0250 | | <0.223 | | |
| *Donor 3* | | | | | | |
| 0 (VC) | 0.02349[a] | <0.0250 | <0.0252 ± 0.000435 | <0.223 | <0.225 ± 0.00388 | 100 |
| | 0.02587 | 0.0259 | | 0.231 | | |
| | 0.02376[a] | <0.0250 | | <0.223 | | |
| | 0.02236[a] | <0.0250 | | <0.223 | | |
| 0.4 | 0.02177[a] | <0.0250 | <0.0250 ± 0.000 | <0.223 | <0.223 ± 0.000 | 99.1 |
| | 0.02343[a] | <0.0250 | | <0.223 | | |
| | 0.02326[a] | <0.0250 | | <0.223 | | |

TABLE 20-continued

CYP2B6 Activity in Cryopreserved Human Hepatocytes

| Metaxalone (µM) | Nirvanol formation | | | Specific Activity | | Percent of VC |
|---|---|---|---|---|---|---|
| | Raw (µM) | Adjusted (µM) | | (pmol/min/million cells) | | |
| | | Individual | Mean ± SD | Individual | Mean ± SD | |
| 4 | 0.02392[a] | <0.0250 | <0.0250 ± 0.000 | <0.223 | <0.223 ± 0.000 | 99.1 |
| | 0.02490[a] | <0.0250 | | <0.223 | | |
| | 0.02229[a] | <0.0250 | | <0.223 | | |
| 40 | 0.02005[a] | <0.0250 | <0.0250 ± 0.000 | <0.223 | <0.223 ± 0.000 | 99.1 |
| | 0.01976[a] | <0.0250 | | <0.223 | | |
| | 0.02169[a] | <0.0250 | | <0.223 | | |

Abbreviations:
SD, standard deviation;
VC, vehicle control (1% Methanol)
[a]The observed analyzed value (µM) was below the lowest concentration on the standard curve (0.025 µM).
Note:
For all calculations above, the resulting values are shown with at least three significant figures for display purposes only.

TABLE 21

CYP2C9 Activity in Cryopreserved Human Hepatocytes

| Metaxalone (µM) | 4'-Methylhydroxytolbutamide formation | | | Specific Activity | | Percent of VC |
|---|---|---|---|---|---|---|
| | Raw (µM) | Adjusted (µM) | | (pmol/min/million cells) | | |
| | | Individual | Mean ± SD | Individual | Mean ± SD | |
| Donor 1 | | | | | | |
| 0 (VC) | 0.01215 | 0.0122 | 0.0137 ± 0.00161 | 0.108 | 0.122 ± 0.0144 | 100 |
| | 0.01502 | 0.0150 | | 0.134 | | |
| | 0.01513 | 0.0151 | | 0.135 | | |
| | 0.01245 | 0.0125 | | 0.111 | | |
| 0.4 | 0.01557 | 0.0156 | 0.0147 ± 0.000753 | 0.139 | 0.132 ± 0.00672 | 108 |
| | 0.01410 | 0.0141 | | 0.126 | | |
| | 0.01455 | 0.0146 | | 0.130 | | |
| 4 | 0.01331 | 0.0133 | 0.0137 ± 0.00136 | 0.119 | 0.122 ± 0.0121 | 100 |
| | 0.01523 | 0.0152 | | 0.136 | | |
| | 0.01261 | 0.0126 | | 0.113 | | |
| 40 | 0.00931[a] | <0.0100 | <0.0100 ± 0.0000346 | <0.0893 | <0.0895 ± 0.000309 | <73.2 |
| | 0.00952[a] | <0.0100 | | <0.0893 | | |
| | 0.01006 | 0.0101 | | 0.0898 | | |
| Donor 2 | | | | | | |
| 0 (VC) | 0.05192 | 0.0519 | 0.0491 ± 0.00479 | 0.464 | 0.438 ± 0.0428 | 100 |
| | 0.04864 | 0.0486 | | 0.434 | | |
| | 0.05325 | 0.0533 | | 0.475 | | |
| | 0.04250 | 0.0425 | | 0.379 | | |
| 0.4 | 0.04819 | 0.0482 | 0.0474 ± 0.00223 | 0.430 | 0.423 ± 0.0200 | 96.6 |
| | 0.04489 | 0.0449 | | 0.401 | | |
| | 0.04915 | 0.0492 | | 0.439 | | |
| 4 | 0.04634 | 0.0463 | 0.0456 ± 0.000864 | 0.414 | 0.407 ± 0.00772 | 92.9 |
| | 0.04581 | 0.0458 | | 0.409 | | |
| | 0.04465 | 0.0447 | | 0.399 | | |
| 40 | 0.02917 | 0.0292 | 0.0296 ± 0.000651 | 0.260 | 0.265 ± 0.00581 | 60.4 |
| | 0.02936 | 0.0294 | | 0.262 | | |
| | 0.03038 | 0.0304 | | 0.271 | | |
| Donor 3 | | | | | | |
| 0 (VC) | 0.02021 | 0.0202 | 0.0181 ± 0.00206 | 0.180 | 0.162 ± 0.0184 | 100 |
| | 0.01700 | 0.0170 | | 0.152 | | |
| | 0.01952 | 0.0195 | | 0.174 | | |
| | 0.01586 | 0.0159 | | 0.142 | | |
| 0.4 | 0.02067 | 0.0207 | 0.0201 ± 0.00125 | 0.185 | 0.179 ± 0.0111 | 111 |
| | 0.02096 | 0.0210 | | 0.187 | | |
| | 0.01867 | 0.0187 | | 0.167 | | |
| 4 | 0.01807 | 0.0181 | 0.0187 ± 0.00235 | 0.161 | 0.167 ± 0.0210 | 103 |
| | 0.02129 | 0.0213 | | 0.190 | | |
| | 0.01671 | 0.0167 | | 0.149 | | |

TABLE 21-continued

CYP2C9 Activity in Cryopreserved Human Hepatocytes

| Metaxalone | 4'-Methylhydroxytolbutamide formation | | | Specific Activity | | Percent |
|---|---|---|---|---|---|---|
| | Raw | Adjusted (µM) | | (pmol/min/million cells) | | |
| (µM) | (µM) | Individual | Mean ± SD | Individual | Mean ± SD | of VC |
| 40 | 0.01364 | 0.0136 | 0.0142 ± 0.000560 | 0.122 | 0.127 ± 0.00500 | 78.4 |
| | 0.01432 | 0.0143 | | 0.128 | | |
| | 0.01475 | 0.0148 | | 0.132 | | |

Abbreviations:
SD, standard deviation;
VC, vehicle control (1% Methanol)
[a]The observed analyzed value (µM) was below the lowest concentration on the standard curve (0.01 µM).
Note:
For all calculations above, the resulting values are shown with at least three significant figures for display purposes only.

TABLE 22

CYP2C19 Activity in Cryopreserved Human Hepatocytes

| Metaxalone | 4'-Hydroxymephenytoin formation | | | Specific Activity | | Percent |
|---|---|---|---|---|---|---|
| | Raw | Adjusted (µM) | | (pmol/min/million cells) | | |
| (µM) | (µM) | Individual | Mean ± SD | Individual | Mean ± SD | of VC |
| Donor 1 | | | | | | |
| 0 | 0.00025[a] | <0.0500 | <0.0500 ± 0.000 | <0.446 | <0.446 ± 0.000 | 100 |
| (VC) | 0.00058[a] | <0.0500 | | <0.446 | | |
| | 0.00114[a] | <0.0500 | | <0.446 | | |
| | 0.00058[a] | <0.0500 | | <0.446 | | |
| 0.4 | 0.00708[a] | <0.0500 | <0.0500 ± 0.000 | <0.446 | <0.446 ± 0.000 | 100 |
| | 0.01319[a] | <0.0500 | | <0.446 | | |
| | 0.01861[a] | <0.0500 | | <0.446 | | |
| 4 | 0.01649[a] | <0.0500 | <0.0500 ± 0.000 | <0.446 | <0.446 ± 0.000 | 100 |
| | 0.00029[a] | <0.0500 | | <0.446 | | |
| | 0.00064[a] | <0.0500 | | <0.446 | | |
| 40 | 0.00057[a] | <0.0500 | <0.0500 ± 0.000 | <0.446 | <0.446 ± 0.000 | 100 |
| | 0.00031[a] | <0.0500 | | <0.446 | | |
| | 0.00037[a] | <0.0500 | | <0.446 | | |
| Donor 2 | | | | | | |
| 0 | N/A* | N/A | <0.0500 ± 0.000 | N/A | <0.446 ± 0.000 | 100 |
| (VC) | 0.01146[a] | <0.0500 | | <0.446 | | |
| | 0.01456[a] | <0.0500 | | <0.446 | | |
| | N/A* | N/A | | N/A | | |
| 0.4 | 0.00765[a] | <0.0500 | <0.0500 ± 0.000 | <0.446 | <0.446 ± 0.000 | 100 |
| | 0.00779[a] | <0.0500 | | <0.446 | | |
| | 0.00808[a] | <0.0500 | | <0.446 | | |
| 4 | 0.00775[a] | <0.0500 | <0.0500 ± 0.000 | <0.446 | <0.446 ± 0.000 | 100 |
| | 0.00744[a] | <0.0500 | | <0.446 | | |
| | 0.00773[a] | <0.0500 | | <0.446 | | |
| 40 | 0.00697[a] | <0.0500 | <0.0500 ± 0.000 | <0.446 | <0.446 ± 0.000 | 100 |
| | 0.00840[a] | <0.0500 | | <0.446 | | |
| | 0.00790[a] | <0.0500 | | <0.446 | | |
| Donor 3 | | | | | | |
| 0 | 0.00026[a] | <0.0500 | <0.0500 ± 0.000 | <0.446 | <0.446 ± 0.000 | 100 |
| (VC) | 0.00000[a] | <0.0500 | | <0.446 | | |
| | 0.00000[a] | <0.0500 | | <0.446 | | |
| | 0.00000[a] | <0.0500 | | <0.446 | | |
| 0.4 | 0.00000[a] | <0.0500 | <0.0500 ± 0.000 | <0.446 | <0.446 ± 0.000 | 100 |
| | 0.00000[a] | <0.0500 | | <0.446 | | |
| | 0.00023[a] | <0.0500 | | <0.446 | | |
| 4 | 0.00000[a] | <0.0500 | <0.0500 ± 0.000 | <0.446 | <0.446 ± 0.000 | 100 |
| | 0.00000[a] | <0.0500 | | <0.446 | | |
| | 0.00000[a] | <0.0500 | | <0.446 | | |

TABLE 22-continued

CYP2C19 Activity in Cryopreserved Human Hepatocytes

| Metaxalone (μM) | 4'-Hydroxymephenytoin formation | | | Specific Activity (pmol/min/million cells) | | Percent of VC |
|---|---|---|---|---|---|---|
| | Raw (μM) | Adjusted (μM) | | | | |
| | | Individual | Mean ± SD | Individual | Mean ± SD | |
| 40 | 0.00191[a] | <0.0500 | <0.0500 ± 0.000 | <0.446 | <0.446 ± 0.000 | 100 |
|  | 0.00000[a] | <0.0500 |  | <0.446 |  |  |
|  | 0.00000[a] | <0.0500 |  | <0.446 |  |  |

Abbreviations:
SD, standard deviation;
VC, vehicle control (1% Methanol)
[a]The observed analyzed value (μM) was below the lowest concentration on the standard curve (0.05 μM).
*Sample lost after preparation.
Note:
For all calculations above, the resulting values are shown with at least three significant figures for display purposes only.

TABLE 23

CYP2D6 Activity in Cryopreserved Human Hepatocytes

| Metaxalone (μM) | Dextrorphan formation | | | Specific Activity (pmol/min/million cells) | | Percent of VC |
|---|---|---|---|---|---|---|
| | Raw (μM) | Adjusted (μM) | | | | |
| | | Individual | Mean ± SD | Individual | Mean ± SD | |
| Donor 1 | | | | | | |
| 0 (VC) | 0.00772[a] | <0.0100 | <0.0100 ± 0.000 | <0.0893 | <0.0893 ± 0.000 | 100 |
|  | 0.00796[a] | <0.0100 |  | <0.0893 |  |  |
|  | 0.00736[a] | <0.0100 |  | <0.0893 |  |  |
|  | 0.00724[a] | <0.0100 |  | <0.0893 |  |  |
| 0.4 | 0.00809[a] | <0.0100 | <0.0100 ± 0.000 | <0.0893 | <0.0893 ± 0.000 | 100 |
|  | 0.00749[a] | <0.0100 |  | <0.0893 |  |  |
|  | 0.00853[a] | <0.0100 |  | <0.0893 |  |  |
| 4 | 0.00832[a] | <0.0100 | <0.0100 ± 0.000 | <0.0893 | <0.0893 ± 0.000 | 100 |
|  | 0.00721[a] | <0.0100 |  | <0.0893 |  |  |
|  | 0.00744[a] | <0.0100 |  | <0.0893 |  |  |
| 40 | 0.00398[a] | <0.0100 | <0.0100 ± 0.000 | <0.0893 | <0.0893 ± 0.000 | 100 |
|  | 0.00205[a] | <0.0100 |  | <0.0893 |  |  |
|  | 0.00520[a] | <0.0100 |  | <0.0893 |  |  |
| Donor 2 | | | | | | |
| 0 (VC) | 0.01286 | 0.0129 | 0.0139 ± 0.00152 | 0.115 | 0.124 ± 0.0136 | 100 |
|  | 0.01432 | 0.0143 |  | 0.128 |  |  |
|  | 0.01581 | 0.0158 |  | 0.141 |  |  |
|  | 0.01247 | 0.0125 |  | 0.111 |  |  |
| 0.4 | 0.01302 | 0.0130 | 0.0133 ± 0.000485 | 0.116 | 0.119 ± 0.00433 | 95.9 |
|  | 0.01302 | 0.0130 |  | 0.116 |  |  |
|  | 0.01386 | 0.0139 |  | 0.124 |  |  |
| 4 | 0.01361 | 0.0136 | 0.0143 ± 0.000589 | 0.122 | 0.128 ± 0.00526 | 103 |
|  | 0.01468 | 0.0147 |  | 0.131 |  |  |
|  | 0.01457 | 0.0146 |  | 0.130 |  |  |
| 40 | 0.00998[a] | <0.0100 | <0.0102 ± 0.000260 | <0.0893 | <0.0906 ± 0.00232 | <73.2 |
|  | 0.00956[a] | <0.0100 |  | <0.0893 |  |  |
|  | 0.01045 | 0.0105 |  | 0.0933 |  |  |
| Donor 3 | | | | | | |
| 0 (VC) | 0.07011 | 0.0701 | 0.0665 ± 0.00607 | 0.626 | 0.594 ± 0.0542 | 100 |
|  | 0.05856 | 0.0586 |  | 0.523 |  |  |
|  | 0.07219 | 0.0722 |  | 0.645 |  |  |
|  | 0.06505 | 0.0651 |  | 0.581 |  |  |
| 0.4 | 0.06218 | 0.0622 | 0.0657 ± 0.00305 | 0.555 | 0.586 ± 0.0272 | 98.8 |
|  | 0.06688 | 0.0669 |  | 0.597 |  |  |
|  | 0.06789 | 0.0679 |  | 0.606 |  |  |
| 4 | 0.06071 | 0.0607 | 0.0597 ± 0.00164 | 0.542 | 0.533 ± 0.0146 | 89.8 |
|  | 0.06060 | 0.0606 |  | 0.541 |  |  |
|  | 0.05782 | 0.0578 |  | 0.516 |  |  |

TABLE 23-continued

CVP2D6 Activity in Cryopreserved Human Hepatocytes

| Metaxalone (μM) | Dextrorphan formation | | | Specific Activity | | Percent of VC |
|---|---|---|---|---|---|---|
| | Raw (μM) | Adjusted (μM) | | (pmol/min/million cells) | | |
| | | Individual | Mean ± SD | Individual | Mean ± SD | |
| 40 | 0.05087 | 0.0509 | 0.0489 ± 0.00347 | 0.454 | 0.436 ± 0.0310 | 73.5 |
| | 0.05088 | 0.0509 | | 0.454 | | |
| | 0.04486 | 0.0449 | | 0.401 | | |

Abbreviations:
SD, standard deviation;
VC, vehicle control (1% Methanol)
[a] The observed analyzed value (μM) was below the lowest concentration on the standard curve (0.01 μM).
Note:
For all calculations above, the resulting values are shown with at least three significant figures for display purposes only.

TABLE 24

CYP2E1 Activity in Cryopreserved Human Hepatocytes

| Metaxalone (μM) | 6-Hydroxychlorzoxazone formation | | | Specific Activity | | Percent of VC |
|---|---|---|---|---|---|---|
| | Raw (μM) | Adjusted (μM) | | (pmol/min/million cells) | | |
| | | Individual | Mean ± SD | Individual | Mean ± SD | |
| Donor 1 | | | | | | |
| 0 (VC) | 0.28067 | 0.281 | 0.283 ± 0.00460 | 2.51 | 2.53 ± 0.0411 | 100 |
| | 0.28793 | 0.288 | | 2.57 | | |
| | 0.28627 | 0.286 | | 2.56 | | |
| | 0.27817 | 0.278 | | 2.48 | | |
| 0.4 | 0.28854 | 0.289 | 0.277 ± 0.0279 | 2.58 | 2.47 ± 0.249 | 97.8 |
| | 0.29749 | 0.297 | | 2.66 | | |
| | 0.24529 | 0.245 | | 2.19 | | |
| 4 | 0.28784 | 0.288 | 0.295 ± 0.0236 | 2.57 | 2.64 ± 0.210 | 104 |
| | 0.27623 | 0.276 | | 2.47 | | |
| | 0.32160 | 0.322 | | 2.87 | | |
| 40 | 0.28453 | 0.285 | 0.294 ± 0.00876 | 2.54 | 2.63 ± 0.0782 | 104 |
| | 0.29753 | 0.298 | | 2.66 | | |
| | 0.30121 | 0.301 | | 2.69 | | |
| Donor 2 | | | | | | |
| 0 (VC) | 0.07385 | 0.0739 | 0.0748 ± 0.00211 | 0.659 | 0.668 ± 0.0188 | 100 |
| | 0.07610 | 0.0761 | | 0.679 | | |
| | 0.07690 | 0.0769 | | 0.687 | | |
| | 0.07229 | 0.0723 | | 0.645 | | |
| 0.4 | 0.07071 | 0.0707 | 0.0776 ± 0.00753 | 0.631 | 0.693 ± 0.0673 | 104 |
| | 0.07649 | 0.0765 | | 0.683 | | |
| | 0.08565 | 0.0857 | | 0.765 | | |
| 4 | 0.06315 | 0.0632 | 0.0670 ± 0.00355 | 0.564 | 0.598 ± 0.0317 | 89.6 |
| | 0.06775 | 0.0678 | | 0.605 | | |
| | 0.07013 | 0.0701 | | 0.626 | | |
| 40 | 0.06247 | 0.0625 | 0.0745 ± 0.0141 | 0.558 | 0.665 ± 0.126 | 99.6 |
| | 0.07091 | 0.0709 | | 0.633 | | |
| | 0.09003 | 0.0900 | | 0.804 | | |
| Donor 3 | | | | | | |
| 0 (VC) | 0.05899 | 0.0590 | 0.0570 ± 0.00420 | 0.527 | 0.509 ± 0.0375 | 100 |
| | 0.06077 | 0.0608 | | 0.543 | | |
| | 0.05718 | 0.0572 | | 0.511 | | |
| | 0.05110 | 0.0511 | | 0.456 | | |
| 0.4 | 0.05031 | 0.0503 | 0.0517 ± 0.00140 | 0.449 | 0.462 ± 0.0125 | 90.7 |
| | 0.05310 | 0.0531 | | 0.474 | | |
| | 0.05169 | 0.0517 | | 0.462 | | |
| 4 | 0.05245 | 0.0525 | 0.0500 ± 0.00389 | 0.468 | 0.446 ± 0.0348 | 87.7 |
| | 0.05202 | 0.0520 | | 0.464 | | |
| | 0.04550 | 0.0455 | | 0.406 | | |

TABLE 24-continued

CYP2E1 Activity in Cryopreserved Human Hepatocytes

| Metaxalone (µM) | 6-Hydroxychlorzoxazone formation | | | Specific Activity | | Percent of VC |
|---|---|---|---|---|---|---|
| | Raw (µM) | Adjusted (µM) | | (pmol/min/million cells) | | |
| | | Individual | Mean ± SD | Individual | Mean ± SD | |
| 40 | 0.05260 | 0.0526 | 0.0535 ± 0.00164 | 0.470 | 0.478 ± 0.0146 | 93.9 |
| | 0.05541 | 0.0554 | | 0.495 | | |
| | 0.05254 | 0.0525 | | 0.469 | | |

Abbreviations:

SD, standard deviation;

VC, vehicle control (1% Methanol)

Note:

For all calculations above, the resulting values are shown with at least three significant figures for display purposes only.

TABLE 25

CYP3A4 Activity in Cryopreserved Human Hepatocytes

| Metaxalone (µM) | 6β-Hydroxytestosterone formation | | | Specific Activity | | Percent of VC |
|---|---|---|---|---|---|---|
| | Raw (µM) | Adjusted (µM) | | (pmol/min/million cells) | | |
| | | Individual | Mean ± SD | Individual | Mean ± SD | |
| Donor 1 | | | | | | |
| 0 (VC) | 0.05693[a] | <0.100 | <0.100 ± 0.000 | <0.893 | <0.893 ± 0.000 | 100 |
| | 0.05726[a] | <0.100 | | <0.893 | | |
| | 0.05367[a] | <0.100 | | <0.893 | | |
| | 0.04590[a] | <0.100 | | <0.893 | | |
| 0.4 | 0.05415[a] | <0.100 | <0.100 ± 0.000 | <0.893 | <0.893 ± 0.000 | 100 |
| | 0.06053[a] | <0.100 | | <0.893 | | |
| | 0.05911[a] | <0.100 | | <0.893 | | |
| 4 | 0.05783[a] | <0.100 | <0.100 ± 0.000 | <0.893 | <0.893 ± 0.000 | 100 |
| | 0.05948[a] | <0.100 | | <0.893 | | |
| | 0.05705[a] | <0.100 | | <0.893 | | |
| 40 | 0.06888[a] | <0.100 | <0.100 ± 0.000 | <0.893 | <0.893 ± 0.000 | 100 |
| | 0.06424[a] | <0.100 | | <0.893 | | |
| | 0.06511[a] | <0.100 | | <0.893 | | |
| Donor 2 | | | | | | |
| 0 (VC) | 0.12401 | 0.124 | <0.117 ± 0.0141 | 1.11 | <1.05 ± 0.126 | 100 |
| | 0.13222 | 0.132 | | 1.18 | | |
| | 0.07973[a] | <0.100 | | <0.893 | | |
| | 0.11219 | 0.112 | | 1.00 | | |
| 0.4 | 0.12083 | 0.121 | 0.134 ± 0.0122 | 1.08 | 1.20 ± 0.109 | >115 |
| | 0.14424 | 0.144 | | 1.29 | | |
| | 0.13828 | 0.138 | | 1.23 | | |
| 4 | 0.10953 | 0.110 | 0.116 ± 0.00524 | 0.978 | 1.03 ± 0.0468 | >98.7 |
| | 0.11883 | 0.119 | | 1.06 | | |
| | 0.11837 | 0.118 | | 1.06 | | |
| 40 | 0.14198 | 0.142 | 0.141 ± 0.00273 | 1.27 | 1.26 ± 0.0244 | >121 |
| | 0.14356 | 0.144 | | 1.28 | | |
| | 0.13824 | 0.138 | | 1.23 | | |
| Donor 3 | | | | | | |
| 0 (VC) | 0.06064[a] | <0.100 | <0.100 ± 0.000 | <0.893 | <0.893 ± 0.000 | 100 |
| | 0.05981[a] | <0.100 | | <0.893 | | |
| | 0.06402[a] | <0.100 | | <0.893 | | |
| | 0.08660[a] | <0.100 | | <0.893 | | |
| 0.4 | 0.05106[a] | <0.100 | <0.100 ± 0.000 | <0.893 | <0.893 ± 0.000 | 100 |
| | 0.08255[a] | <0.100 | | <0.893 | | |
| | 0.05998[a] | <0.100 | | <0.893 | | |
| 4 | 0.06298[a] | <0.100 | <0.100 ± 0.000 | <0.893 | <0.893 ± 0.000 | 100 |
| | 0.05381[a] | <0.100 | | <0.893 | | |
| | 0.07264[a] | <0.100 | | <0.893 | | |

TABLE 25-continued

CYP3A4 Activity in Cryopreserved Human Hepatocytes

| Metaxalone (µM) | 6β-Hydroxytestosterone formation | | | Specific Activity (pmol/min/million cells) | | Percent of VC |
|---|---|---|---|---|---|---|
| | Raw (µM) | Adjusted (µM) | | | | |
| | | Individual | Mean ± SD | Individual | Mean ± SD | |
| 40 | 0.05587[a] | <0.100 | <0.101 ± 0.00238 | <0.893 | <0.905 ± 0.0213 | 101 |
| | 0.10413 | 0.104 | | 0.930 | | |
| | 0.08088[a] | <0.100 | | <0.893 | | |

Abbreviations:
SD, standard deviation;
VC, vehicle control (1% Methanol);
[a]The observed analyzed value (µM) was below the lowest concentration on the standard curve (0.1 µM).
Note:
For all calculations above, the resulting values are shown with at least three significant figures for display purposes only.

Table 18 presents the results for CYP1A2. Under these experimental conditions, exposure to metaxalone at 40 µM induced CYP1A2 activity in human hepatocytes prepared from Donors 1, 2, and 3. For each of the three donors, the increases in CYP1A2 activity by metaxalone at 0.4 and 4 µM were not statistically significant (p>0.05; unpaired two-tailed t test).

Table 25 presents the results for CYP3A4. Metaxalone at the concentration of 40 µM induced CYP3A4 activity by about 21% in one of three donors tested, Donor 2. Therefore under these experimental conditions, exposure to metaxalone at 40 µM induced CYP3A4 activity in human hepatocytes prepared from Donor 2. The increase in CYP3A4 activity following treatment with metaxalone at 0.4 µM for Donor 2 was not statistically significant (p>0.05; unpaired two-tailed t test). CYP3A4 activity in the vehicle controls for Donor 1 and Donor 3 were below the lower limit of quantitation. Exposure of hepatocytes from Donors 1 and 3 to metaxalone at the concentrations tested did not induce CYP3A4 activity since the activity following treatment with metaxalone was still below the lower limit of quantitation at each tested concentration.

Table 21 presents the results for CYP2C9. Under these experimental conditions, exposure to metaxalone at 40 µM significantly reduced CYP2C9 activity in human hepatocytes prepared from Donors 1, 2, and 3. The observed changes in CYP2C9 activity following exposure to metaxalone at 0.4 and 4 µM were not statistically significant (p>0.05; two-tailed t test). Thus, under these experimental conditions, exposure to metaxalone at 40 µM inhibited CYP2C9 activity.

Table 23 presents the results for CYP2D6. CYP2D6 activity was below the lower limit of quantitation in the vehicle controls and for the metaxalone-exposed samples for Donor 1. However, under these experimental conditions, exposure to metaxalone at 40 µM significantly reduced CYP2D6 activity in human hepatocytes prepared from Donors 2 and 3. The observed changes in CYP2D6 activity following exposure to metaxalone at 0.4 and 4 µM were not statistically significant (p>0.05; two-tailed t test). Thus, under these experimental conditions, exposure to metaxalone at 40 µM inhibited CYP2D6 activity.

Any combination of the above-described elements in all possible variations thereof is encompassed by the invention unless otherwise indicated herein or otherwise clearly contradicted by context.

We claim:

1. A method of using metaxalone for treating a musculoskeletal condition, comprising
   administering to a human patient metaxalone and an inhibitor or an inducer of CYP1A2;
   informing the human patient that metaxalone is a substrate of CYP1A2 and that administration of metaxalone and an inhibitor or an inducer of CYP1A2 can affect plasma concentration, bioavailability, safety, efficacy, or a combination comprising at least one of the foregoing of metaxalone; and
   monitoring the human patient's plasma concentration of metaxalone while metaxalone and the inhibitor or the inducer of CYP1A2 are administered to the human patient.

2. The method of claim 1, additionally comprising
   altering dosing of metaxalone based on the human patient's plasma concentration of metaxalone.

3. The method of claim 1, wherein an inhibitor of CYP1A2 is administered to the human patient and the inhibitor of CYP1A2 is amiodarone, cimetidine, a fluoroquinolone, fluvoxamine, furafylline, interferon, methoxsalen, or mibefradil.

4. The method of claim 1, wherein an inducer of CYP1A2 is administered to the human patient and the inducer of CYP1A2 is insulin, methyl cholanthrene, modafinil, nafcillin, beta-naphthoflavone, or omeprazole.

5. A method of using metaxalone for treating a musculoskeletal condition, comprising
   administering to a human patient metaxalone and an inhibitor or an inducer of CYP2C19;
   informing the human patient that metaxalone is a substrate of CYP2C19 and that administration of metaxalone and an inhibitor or an inducer of CYP2C19 can affect plasma concentration, bioavailability, safety, efficacy, or a combination comprising at least one of the foregoing of metaxalone; and
   monitoring the human patient's plasma concentration of metaxalone while metaxalone and the inhibitor or the inducer of CYP2C19 are administered to the human patient.

6. The method of claim 5, additionally comprising
   altering dosing of metaxalone based on the human patient's plasma concentration of metaxalone.

7. The method of claim 5, wherein an inhibitor of CYP2C19 is administered to the human patient and the inhibitor of CYP2C19 is chloramphenicol, cimetidine, felbamate, fluoxetine, fluvoxamine, indomethacin, ketoconazole, lansoprazole, modafinil, omeprazole, oxcarbazepine, probenicid, ticlopidine, or topiramate.

8. The method of claim 5, wherein an inducer of CYP2C19 is administered to the human patient and the inducer of CYP2Cl9 is carbamazepine, norethindrone, prednisone, or rifampicin.

* * * * *